United States Patent [19]
Burton et al.

[11] Patent Number: 5,496,271
[45] Date of Patent: Mar. 5, 1996

[54] COMBINED HYPERTHERMIA AND DILATION CATHETER

[75] Inventors: John H. Burton, Minnetonka; Timothy C. Cook, Wayzata; Claude Tihon, Eden Prairie, all of Minn.

[73] Assignee: American Medical Systems, Inc., Minnetonka, Minn.

[21] Appl. No.: 78,367

[22] Filed: Jun. 16, 1993

Related U.S. Application Data

[63] Continuation-in-part of Ser. No. 582,726, Sep. 14, 1990, abandoned.

[51] Int. Cl.$^6$ .................................... A61H 31/00
[52] U.S. Cl. .................. 604/54; 604/101; 604/113; 606/27; 607/102; 607/113; 607/143
[58] Field of Search ................... 604/20, 53–54, 604/96, 101, 113–114; 606/27–31; 607/96, 101–102, 113–116, 138, 143

[56] References Cited

U.S. PATENT DOCUMENTS

| | | | |
|---|---|---|---|
| 2,799,273 | 7/1957 | Oddo | 604/101 |
| 4,662,383 | 5/1987 | Sogawa et al. | 128/784 |
| 4,932,956 | 6/1990 | Reddy et al. | 606/192 |
| 5,007,437 | 4/1991 | Sterzer | 128/786 |

*Primary Examiner*—Corrine M. McDermott
*Attorney, Agent, or Firm*—Peter C. Richardson; Lawrence C. Akers; Howard R. Jaeger

[57] ABSTRACT

An apparatus and method for treatment of conditions in which it is desired to simultaneously hyperthermally treat diseased target tissue in a patient and dilate a lumen of a patient which is compressed and/or obstructed by the diseased target tissue and/or surrounding tissue is disclosed. The apparatus generally includes a catheter for insertion into a lumen of the patient, such as in the prostatic urethra; an antenna for applying microwave or radio frequency energy to the selected target tissue to produce hyperthermal effects therein, thereby causing therapeutic alteration of the selected target tissue cells; a dilation balloon for simultaneously dilating the lumen of the patient and for compressing tissue to restrict blood flow to said tissue, thereby reducing the heat sink effect of blood-supplied tissue absorbing heat energy applied thereto, enabling both greater uniformity of heating in selected target diseased tissue and a reduction in the amount of power required to supply an effective level of energy to the selected target diseased tissue; and a fixation balloon for securing the apparatus during treatment. The apparatus and method are particularly adapted to the treatment of diseases of the prostate, such as benign prostatic hypertrophy (BPH), prostatitis and prostatic cancer, as well as in the treatment of certain tumors of the esophagus and the gastro-intestinal tract.

34 Claims, 19 Drawing Sheets

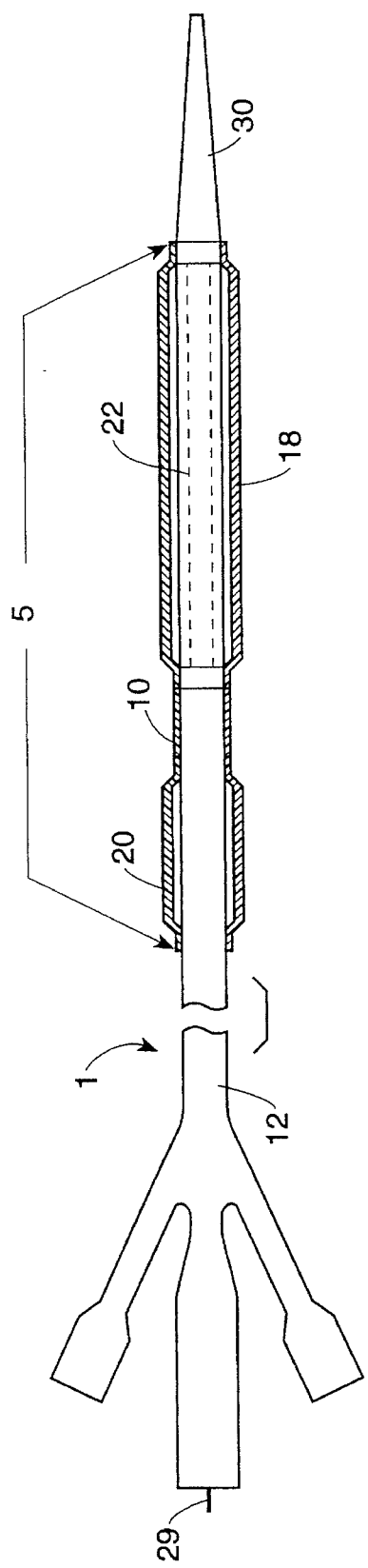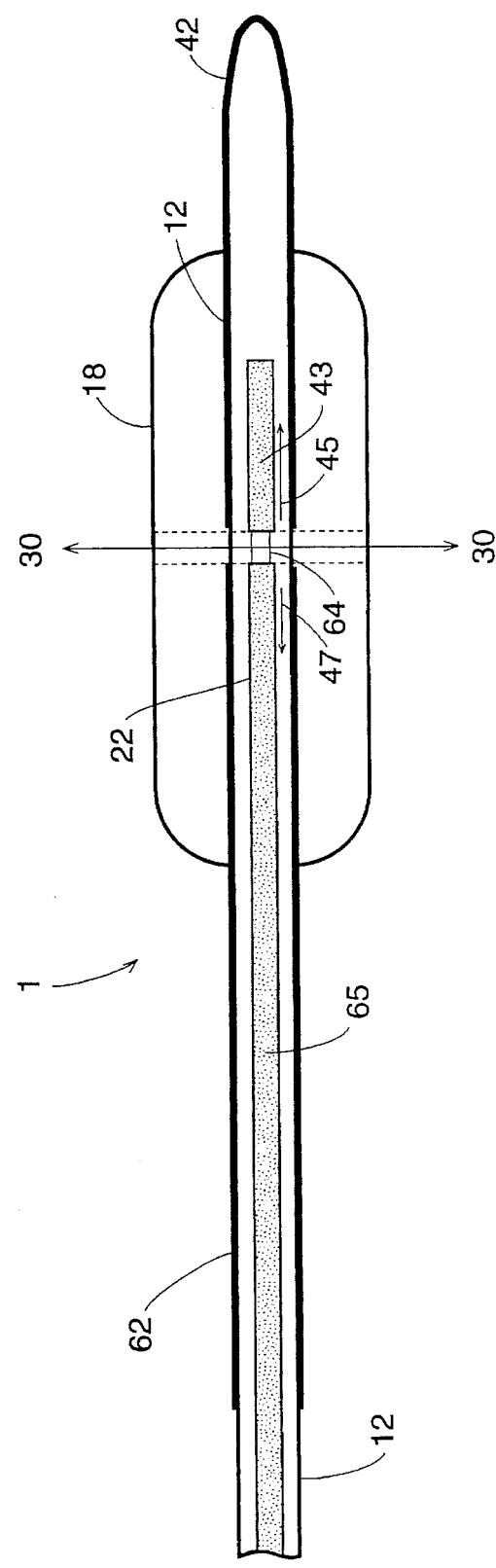

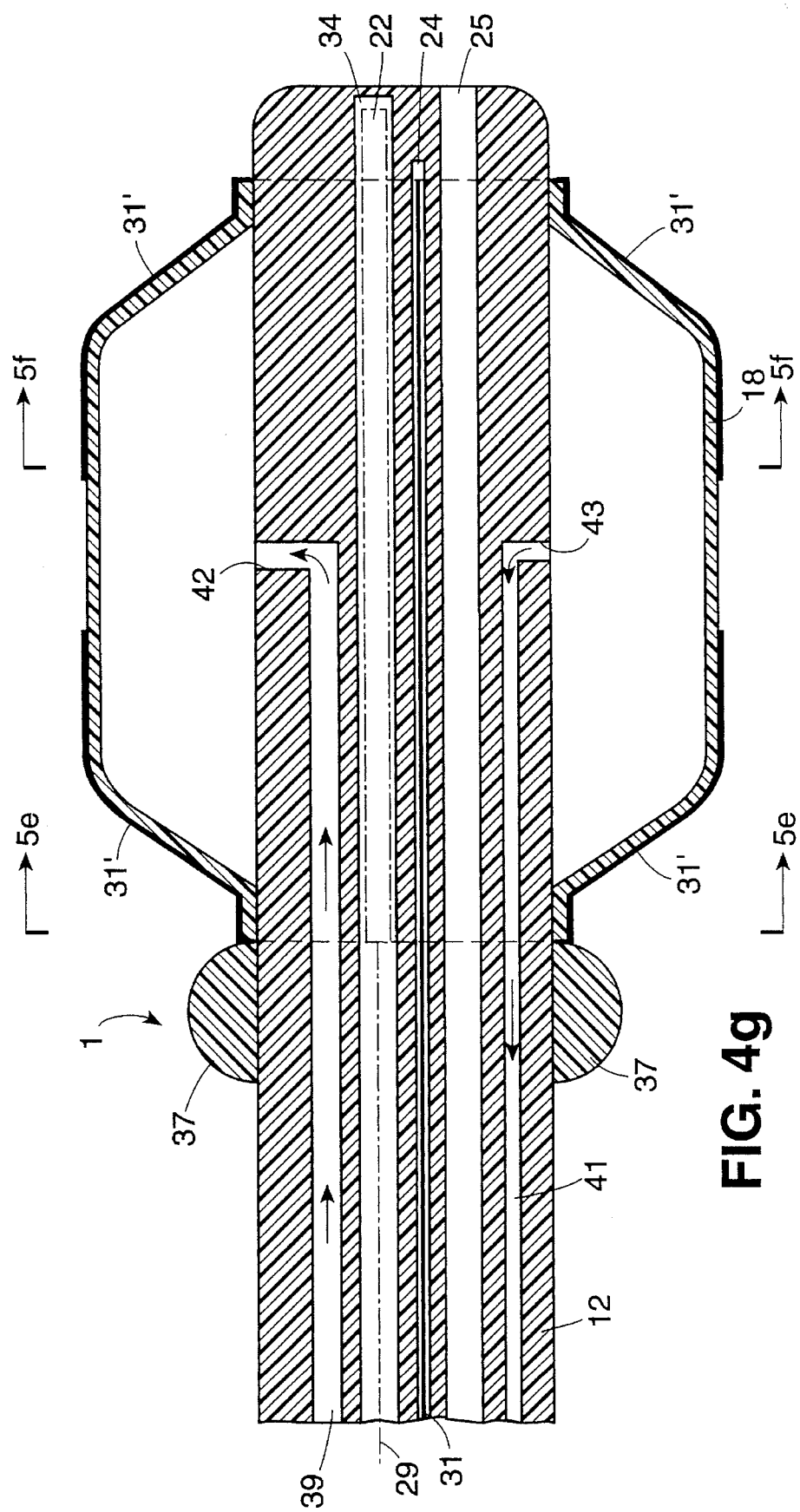

COMBINED HYPERTHERMIA AND DILATION CATHETER

This is a Continuation-In-Part of application Ser. No. 07/582,726, filed Sep. 14, 1990, now abandoned.

FIELD OF THE INVENTION

This invention relates to an apparatus and method for the treatment of conditions in which it is desired to simultaneously hyperthermally treat diseased target tissue in a patient and dilate a lumen of a patient which is being compressed and obstructed by diseased tissue and/or surrounding tissue, especially as such a state exists in diseases of the prostate, including benign prostatic hypertrophy (BPH), and in other conditions of the prostate, such as prostatitis, and prostatic cancer, as well as in certain tumors of the esophagus and the gastro-intestinal tract. In particular, the invention relates to a catheter featuring the combined use of microwave or radio frequency hyperthermia and balloon dilation.

BACKGROUND OF THE INVENTION

Prostatic disease is one of the most common diseases in men in the United States. Prostatic disease, as referred to here, includes benign prostatic hypertrophy (BPH), prostatitis, and prostatic cancer. These etiologies affect a majority of men over the age of 60.

Although the size of the prostate does not reflect the severity of BPH symptoms, it is clear that hypertrophy of the prostate gland and/or hyperplasia of stromal tissue cells is involved.

The currently accepted treatment for BPH is transurethral resection of the prostate (TURP). Approximately 400,000 TURPs per year are performed to treat this disorder in the United States. Morbidity and mortality for TURP are 17 and 1 percent, respectively, for all age groups. Higher complication rates occur in older populations with an annual surgical and hospitalization cost in excess of $1 billion per year.

Thus, TURP may only be applicable to patients who are not at risk for surgical complications. Among other treatments available for the condition of BPH are pharmacological means such as vasoactive and antiandrogen agents.

The etiology of prostatitis, which is an inflammation of the prostate, is not entirely known, except that in about 20% of cases, where it is bacterially induced.

With regard to prostatic cancer, both the incidence and mortality are on the rise. It is expected that over 134,000 new cases will be diagnosed this year alone, with some 33,000 cases proving fatal.

While the etiology of prostatic cancer is also not well known, it has been suggested that this disease is either biochemically or genetically induced. The symptoms of prostatic cancer are often insidious and may not be clinically manifest until the course of the disease is advanced. The current treatment of choice for prostatic cancer is surgery which may involve excision of the prostate gland.

There is a need in the field of treatment of prostatic disease, both benign and cancerous, for an effective, less invasive alternative means of treatment to the more invasive, and consequently more complicated and more dangerous surgical procedures which currently are the treatments of choice, namely, TURP for BPH and radical prostatectomy for prostatic cancer.

In prostatic diseases, reduction in the diameter of the lumen, i.e., the prostatic urethra, is externally induced by compression on the luminal wall due to the proliferation of epithelial and stromal cell tissue, which is benign in the case of BPH and cancerous in prostatic cancer. This reduction in luminal diameter causes clinical symptoms for the patient during urination. In order to be effective, treatment of BPH must cause a reduction in the mass of the prostatic tissue responsible for creating the compressive forces on the urethra which results in the obstruction of flow through the lumen of the urethra. This is accomplished either by surgical excision of the tissue or by other means which will cause changes in the cells with therapeutic effects.

The use of dilation alone has been known in the art of treatment of BPH. Dilation of a prostatic urethra which has become compressed and obstructed by external forces due to a proliferation of diseased prostate tissue cells, however, is useful in alleviating symptoms only in the short term. Unfortunately in the majority of cases it has been observed that recompression and obstruction of the prostatic urethra, accompanied by a recurrence of the symptoms, occurs within a relatively short period of time, requiring that the entire procedure be repeated, which entails considerable expense and inconvenience to the patient. Accordingly, alternative modes of therapy have been sought which can afford more long lasting or permanent cure of remission from the disease and relief of the symptoms. U.S. Pat. Nos. 4,932,956 and 4,932,958 both to Reddy et al., both for Prostate Balloon Dilator, and both assigned to the assignee of the present invention, disclose catheters which utilize balloon dilation to expand the lumen of the prostatic urethra. These two patents are incorporated herein by reference.

The use of hyperthermia alone is known in the treatment of tumors and lesions.

U.S. Pat. No. 4,662,383 to Sogawa et al. for Endotract Antenna Device for Hyperthermia discloses an apparatus incorporating a microwave radiation antenna surrounded by a balloon-like member with circulation of a cooling liquid to and from the inside of the balloon-like member, for treating endotract lesions. The balloon of this apparatus is made of a material which is deformable to form an intimate fitting with the inner surface of the wall of the tract organ. The balloon of this apparatus, therefore, cannot be used to dilate the lumen of a vessel, such as the prostatic urethra, which has become obstructed by external compression due to a hypertrophied prostate.

Similarly, published European Patent Application No. 370,890 of Technomed discloses an apparatus for the treatment of tissue, such as of the prostate, by hyperthermia. The apparatus includes means for providing hyperthermal energy, such as microwave energy supplied to and emitted from an antenna in the apparatus, together with heat protection means which generally constitutes means forming a radio-reflecting screen, and which according to certain embodiments contains a radio-reflecting liquid medium. According to some embodiments, the liquid-filled screen is a balloon at the front end of the microwave antenna. In those embodiments incorporating a balloon, however, as in Sogawa et al., the balloon is not designed to also dilate an obstructed lumen of a vessel such a an externally constricted prostatic urethra.

The combined use of dilation and hyperthermia has been suggested for treatment of obstructive atheromatous plaque in cardiovascular disease. The etiology of cardiovascular disease is, however, markedly different from that of prostatic diseases.

In cardiovascular disease the source of the obstruction of the lumen is internal to the lumen itself, namely, the deposits of atheromatous plaque on the wall of the vessel. The objective of the apparatus and methods used in the treatment of cardiovascular disease is to widen the lumen of a vessel by pushing away the internally obstructive material.

U.S. Pat. No. 4,643,186 to Rosen et al. for Percutaneous Transluminal Microwave Catheter Angioplasty, and West German Laid-Open Patent Application No. DE 3743578 A1 to Zeiher for Balloon Catheter for Recanalization of Stenoses in Body Channels, in Particular Coronary Vessels and Peripheral and Arterial Vessels, disclose catheters each having at least one embodiment thereof featuring balloon dilation to mechanically displace plaque deposits on the inner surface of a vessel wall to expand the lumen of the vessel, and the application of microwave energy to the plaque to soften, coagulate, and/or electroablate the plaque, to further expand the effective cross-sectional area of the lumen of the vessel available for flow through the vessel.

U.S. Pat. No. 4,799,479 to Spears for Method and Apparatus for Angioplasty, discloses a device utilizing balloon dilation and the application of thermal energy supplied by means of a laser. Balloon inflation is used to facilitate fusion of disrupted plaque, which, together with arterial wall tissue, is heated and fused together to form a smooth, cylindrically-shaped channel in the lumen of the vessel which is resistant to restenosis.

Hyperthermia has also been used in conjunction with chemotherapy and/or radiation therapy in cancer treatment with the expectation that the elevated temperature increases the therapeutic index. Hyperthermia is also a means for treatment of other, non-cancerous, benign conditions such as BPH and prostatitis.

From in vitro studies it has been observed that in order for hyperthermia to be effective, the temperature of all the target cells must be raised to a minimum of 42.5° C. and maintained at least at that temperature for a sufficient period of time to cause cell changes. Recent in vivo studies an animals suggest that a temperature of around 48° C. must be attained and maintained in target diseased tissue cells for hyperthermia to be effective.

The use of hyperthermia in the treatment of various forms of cancer, including prostatic cancer, has been attempted for some time. However, this therapy has met with only limited effectiveness due to the fact that blood flow to the target cells is not reduced and may, in fact, increase. Because of blood flow, a heat sink phenomenon occurs which reduces the thermal energy delivered to the target cells, thus reducing the magnitude and uniformity of heating and cell destruction.

Published PCT Patent Application WO 90/13333 of Intra-Sonix discloses an instrument and method for dilating a stenotic region of a passageway in the body, such as the prostatic urethra. Selected portions of prostate tissue are compressed, such as by using a balloon inserted in the prostatic urethra to enhance hemostatis, and selected portions of the compressed tissue are denatured, such as by exposure to laser energy. The pressure to which the balloon of this apparatus is inflated is just sufficient to compress the prostate tissue without necessarily exceeding the elastic limit of the tissue, as is required in a balloon dilation procedure.

Another previously known device has sought to combine dilation with microwave hyperthermia.

U.S. Pat. No. 5,007,437 to Sterzer for Catheter for Treating Prostate Disease discloses a urethral and/or rectal catheter incorporating an inflatable prostate balloon to compress the prostate while it is being irradiated from a microwave antenna. The apparatus is said to enable an increase in the therapeutic temperature to which the prostate tissue distal to the microwave antenna can be heated without heating any non-prostate tissue beyond a maximum safe temperature, and reduces the temperature differential between the heated prostate tissue more distal from and more proximate to the microwave antenna. The catheter includes a Foley balloon near the distal end of the catheter, forward of the prostate balloon, to fix the catheter in place.

Published PCT Patent Application WO 91/11975 of Technomed discloses an apparatus for the treatment of tissue, such as of the prostate, by hyperthermia and includes means for dilation. This apparatus includes means for providing microwave energy for hyperthermia, a dilation balloon toward the distal end of the apparatus, and fixation balloons both distal and proximal to the dilation balloon. The forward fixation balloon, distal to the dilation balloon, is positioned in the bladder. The dilation balloon is used to dilate the prostatic urethra, however, the disclosure suggests that dilation is used principally to dilate the lumen to compress tissue between the lumen wall and more remote tissue to be treated by hyperthermia. Nothing is disclosed about the ability of the dilation balloon to also dilate the bladder neck in the treatment of prostate disease.

It is desirable to have an alternative apparatus and method of treatment that is readily adaptable for use in the treatment of any condition in which it is desired to simultaneously hyperthermally treat diseased target tissue in a patient and dilate a lumen of a patient which is being compressed and obstructed by diseased tissue and/or surrounding tissue, particularly, such as exists in diseases of the prostate, and in certain tumors of the esophagus and the gastro-intestinal tract; and which is less invasive than surgery, is capable of producing longer term results than dilation alone, and overcomes the limited effectiveness of previously known devices and methods which utilize hyperthermia either alone or in combination with dilation, by overcoming the heat sink phenomenon, and by enabling dilation of an obstructed lumen to produce a dilated condition of the lumen which will persist for a time after removal of the apparatus from the lumen. In the case of treatment of prostate disease, in particular, it is desirable to provide an apparatus which is capable of providing hyperthermal therapy, while also simultaneously dilating both the prostatic urethra and the bladder neck.

Accordingly, it is an object of the present invention to provide an apparatus and method for the treatment of conditions in which it is desired to simultaneously hyperthermally treat diseased target tissue in a patient and dilate a lumen of a patient which is being compressed and obstructed by diseased tissue and/or surrounding tissue. It is another object of the present invention to fill the need in the art of treatment of prostate disease with an apparatus and a method for its use that combines the use of hyperthermia together with the use of balloon dilation for the treatment of both benign and cancerous forms of prostate disease, and other conditions and diseases resulting in an enlarged prostate, to achieve both the short term benefits of dilation therapy and the long term benefits of hyperthermal therapy. It is still another object of the present invention to provide an apparatus and method for the treatment of prostate diseases, which in delivering dilation mode therapy, is capable of simultaneously dilating both an obstructed prostatic urethra and the bladder neck to relieve the symptom of inability to urinate characteristic of prostate diseases. It is a further object of the present invention to provide an apparatus and method which combines the two treatment modalities of hyperthermia and dilation in such a way that the heat sink phenomenon associated with hyperthermal treatment is reduced and a synergistic result is obtained. It is a still further object of the present invention to provide an apparatus which is an improvement over previously known apparatus in that it is easier and more economical to construct, and is partially reusable, requiring only replacement of the outer parts which come in patient contact.

SUMMARY OF THE INVENTION

The present invention provides an apparatus and method for treatment of conditions in which it is desired to simultaneously hyperthermally treat diseased target tissue in a patient and dilate a lumen of a patient which is being compressed and obstructed by the diseased target tissue and/or surrounding tissue. The apparatus and method are particularly adapted to the treatment of prostate disease, both benign and cancerous. The apparatus and method are also adaptable to the treatment of other conditions having similar etiologies and/or symptoms, including, but not limited to, tumors of the esophagus and/or gastro-intestinal tract. In the treatment of prostate diseases, the apparatus and method of the present invention utilize the application of hyperthermal therapy to produce long term effects in diseased tissue cells in combination with dilation to dilate the prostatic urethra and bladder neck, and enhance performance of the hyperthermal therapy by restricting blood flow to reduce or eliminate the heat sink effect which otherwise attenuates the effect of the hyperthermal treatment.

For the treatment of BPH in particular, both dilation and hyperthermia have a direct effect in alleviating the symptoms of the disease. For the treatment of prostatic cancer, the contribution of the effects of dilation alone are not fully understood, and will not be markedly evident in alleviating symptoms unless the course of the disease has progressed to the extent that the proliferation of cancerous prostatic cells is large enough to exert a compressing force on the prostatic urethra causing an acute obstruction of the prostatic urethra. In the treatment of all forms of prostatic disease however, the dilation mode of therapy also enhances the efficacy of the hyperthermal mode of treatment by restricting blood to the target tissue thereby reducing the heat sink effect and allowing the transfer of heat energy to be more readily and uniformly absorbed by the target tissue to produce hyperthermal effects therein.

The heat sink effect is an effect wherein blood-supplied tissue, both healthy and diseased, tends to absorb heat energy in order to dissipate the heat and prevent damage to the tissue. The effect is the result of the high heat capacity of blood. As a natural body safety mechanism to protect healthy tissue, the effect is important to maintaining viability of the tissue and is desirable. In the case of treatment of diseased tissue, which is being hyperthermally treated to destroy the diseased cells, however, the effect is undesirable because both blood-supplied target diseased tissue being treated as well as surrounding blood-supplied healthy tissue tend to dissipate the heat energy intended to be applied to the selected target diseased tissue, thereby requiring the application of increasingly greater power levels to supply an effective level of energy to the target diseased tissue to produce hyperthermal effects therein and achieve a therapeutic result of altering the target diseased tissue cells. This heat sink effect is greatly reduced when blood flow to both the target diseased tissue and the surrounding healthy tissue is temporarily reduced or cut off, because the heat absorbing capacity of tissue unsupplied with blood is significantly reduced. The reduction or cut-off of the blood supply to the tissue is done for a sufficiently long period of time to enable treatment of the diseased tissue. The temporary application of pressure to the tissue is sufficient to cause a reduction in blood flow to the tissue. In the treatment of diseases of the prostate with the apparatus of the present invention, this is conveniently achieved utilizing the dilation balloon, which when inflated to proper pressure, both dilates an obstructed prostatic urethra and also causes a reduction in blood flow to all tissue being compressed, both the target diseased prostatic tissue as well as surrounding healthy prostatic and urethral tissue and tissue of the urothelium, the lining between the prostate and the urethra. This enables a more effective hyperthermal treatment of diseased tissue utilizing minimum power consumption.

The apparatus of the present invention has the advantages of being able to dilate both the prostatic urethra and the bladder neck. Because the dilation balloon is situated near the distal end of the catheter, when the catheter is positioned such that the distal end thereof extends through the bladder neck and beyond into the bladder, a portion of the dilation balloon is positioned in the prostatic urethra and another portion through the bladder neck and into the bladder. The resultant widening of both the prostatic urethra and bladder neck helps to alleviate the inability to urinate symptom associated with prostate diseases.

Because the distal end of the catheter and part of the dilation balloon extend beyond the bladder neck and into the bladder itself, the heating means for hyperthermal treatment is also in proximity to the median lobe of the prostate which lies adjacent to the bladder beyond the bladder neck. In advanced cases of BPH and prostatic cancer, where extensive hyperplasia of prostatic tissue cells in both the transverse lobes of the prostate, which surround the prostatic urethra, and the median lobe of the prostate adjacent the bladder has occurred, it is essential that hyperthermal therapy be capable of being directed toward all parts of the prostate requiring treatment. Heretofore, most devices have been designed in such a way that when in position they are only able to effect treatment of the transverse lobes of the prostate immediately adjacent to the prostatic urethra, while not being able to permit hyperthermal energy from reaching the median lobe.

An apparatus for treatment of diseases of the prostate according to the present invention generally includes an outer catheter having a distal end, a proximal end having a plurality of ports therein, and a plurality of lumens and/or channels extending axially through the outer catheter, such lumens including a lumen adapted for carrying heating means and lumens adapted for carrying a fluid into and out of at least one of an inflatable dilation balloon and an inflatable fixation balloon, the fluid being for the inflation of the balloons and alternatively also for acting as a coolant. There may also be up to one or more separate lumens adapted for performing one or more of the functions of carrying temperature sensing means; circulating a coolant fluid through the outer catheter when the fluid for the inflation of the dilation and fixation balloons is not also a coolant; carrying catheter guiding means; and for drainage of fluid from the bladder. In certain embodiments, lumens may be multi-functional. There is generally a corresponding port in the proximal end of the outer catheter which cooperates with each lumen in the outer catheter. An apparatus also generally includes heating means, axially mounted within the distal end of the outer catheter in a lumen provided therefor, for applying energy to selected diseased prostate target tissue to produce hyperthermal effects therein, thereby causing a therapeutic alteration of cells in the target tissue; an inflatable dilation balloon mounted at the distal end of the outer catheter for enlarging an obstructed lumen of the prostatic urethra by compressing obstructive prostatic tissue, and for restricting blood flow to at least one of said target tissue and to non-target tissue in the vicinity of said target tissue, in order to reduce the energy absorbing heat sink effect produced by blood-enriched tissue, thereby causing a more complete and more uniform absorption of energy by the target tissue. The dilation balloon has a preform diameter, and an oriented diameter greater than the preform diameter, such that the ratio of the oriented diameter to the preform diameter is from about 4.0 to about 7.0. The dilation balloon also has a preform length and an oriented length greater than the preform length, such that the ratio of the oriented length to the preform length is from about 1.5 to about 3.0. The dilation balloon is fabricated from a material which imparts sufficient hoop strength and burst pressure to the balloon to enable it to perform its intended function, while being bio-compatible and having sufficient softness and pliability to prevent damage to the urothelium with which it comes into contact. An apparatus also generally includes an inflatable fixation balloon mounted towards the distal end of the outer catheter adjacent to the dilation balloon, a distance along the length of the outer catheter in a direction toward the proximal end of the outer catheter. The fixation balloon has a preform diameter, and an oriented diameter greater than the preform diameter, such that the ratio of the oriented diameter to the preform diameter is from about 4.0 to about 7.0. The fixation balloon also has a preform length and an oriented length greater than the preform length, such that the ratio of the oriented length to the preform length is from about 1.5 to about 3.0. The fixation balloon is fabricated from a material which imparts sufficient hoop strength and burst pressure to the balloon to enable it to perform its intended function, while being bio-compatible and having sufficient softness and pliability to prevent damage to tissue with which it comes into contact. Finally, an apparatus generally includes temperature sensing means together with a temperature signal transmitting lead attached at one end thereof to the temperature sensing means. The lead passes through a lumen in the outer catheter provided therefor, and exits from the proximal end of the outer catheter, at which an opposite end of the lead is connected to means for indicating temperature readings measured by the temperature sensing means. In a preferred embodiment of the apparatus, the outer catheter is flexible, the fixation means is a fixation balloon, the dilation means is a dilation balloon and the heating means is a microwave antenna.

Other alternative embodiments of the apparatus incorporate one or more additional features including cooling means for temperature moderation of the heating means to prevent overheating and for cooling the urothelium adjacent to the prostatic urethra to prevent damage to the tissue of the urothelium; catheter guidance means to facilitate insertion of the apparatus and increase its stiffness; a protuberance on the catheter tube, capable of being rectally palpated by the physician to assist in positioning of the apparatus; and feedback circuit means for regulating the amount of energy provided by the heating means.

BRIEF DESCRIPTION DRAWINGS

FIG. 3b is a sectional view of an embodiment of the apparatus having a single piece dilation balloon and fixation balloon.

FIG. 4g is a cross-sectional view of the distal end of an embodiment of the device according to the present invention, having a thermocuople attached to the outer surface of the dilatio balloon.

FIG. 5a is a cross-sectional end view of the apparatus through location 5a—Sa of FIG. 4a.

FIGS. 7a–e show alternative configurations of lumens and channels in the outer catheter according to embodiments of the present invention.

FIG. 8 shows microwave shielding on a combined dilation balloon and hyperthermia catheter according to the present invention.

Figure 9A:
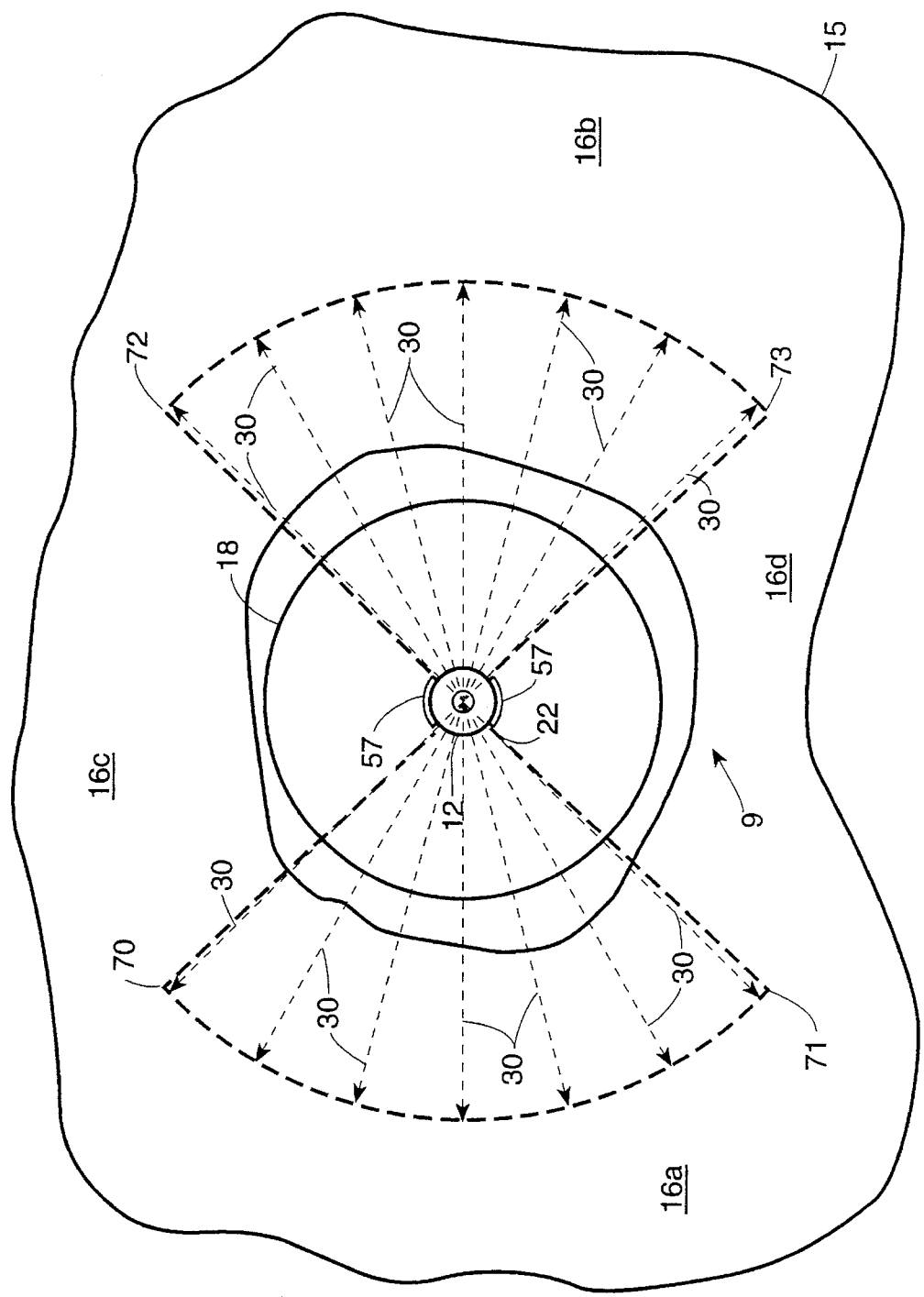
Figure 9B:
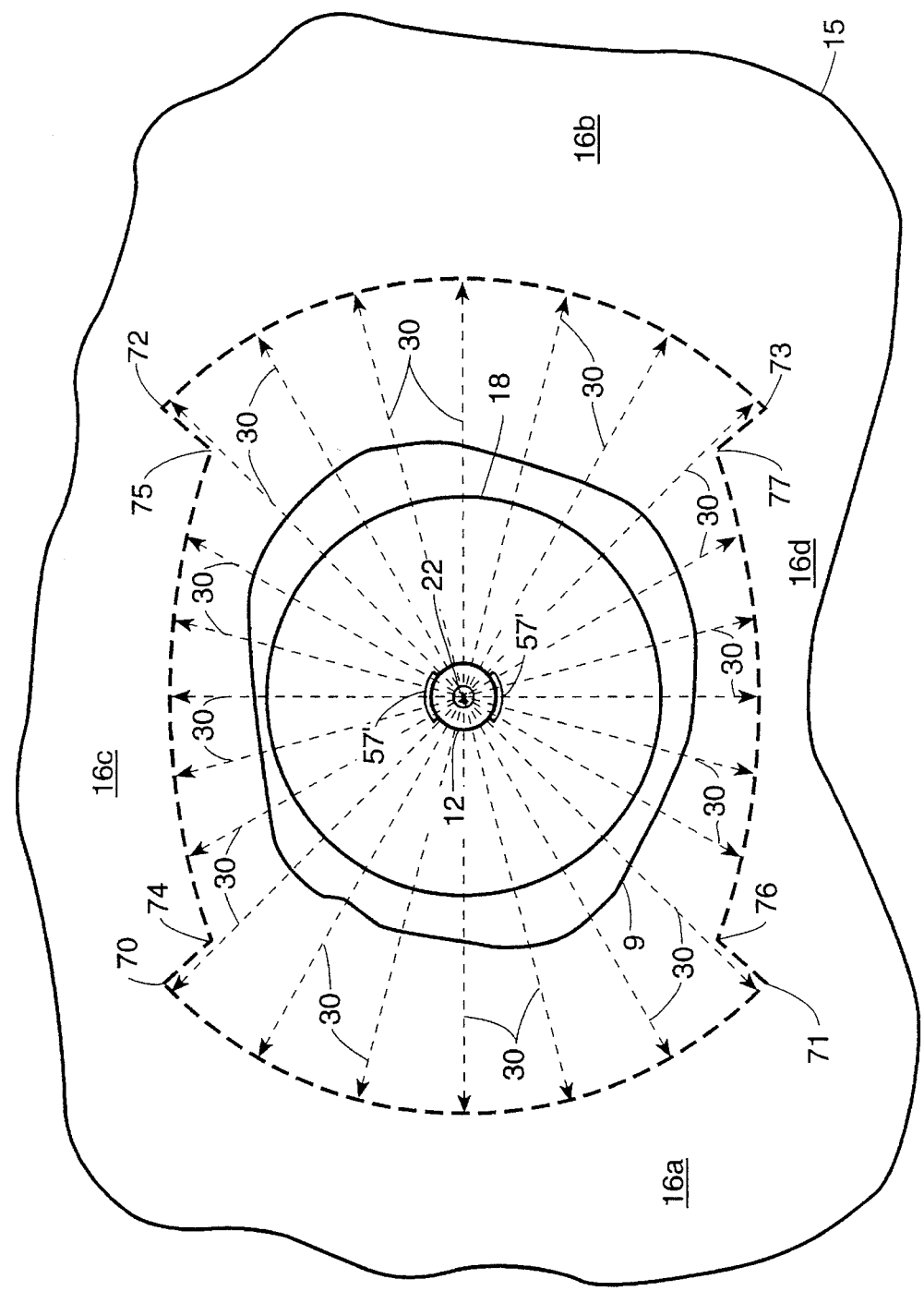

FIGS. 9a–b show microwave energy field patterns emanating from full and partially shielded catheters according to the present invention.

DETAILED DESCRIPTION OF THE INVENTION

As used hereinafter, the term proximal refers to an orientation towards the end of the apparatus external to the lumen of the patient, e.g., the urethra, and nearest the operator of the apparatus, and distal refers to an orientation towards the end of the apparatus which is inserted into the lumen of the patient in a direction which is more internal to the patient, e.g., the urethra, in the direction nearest to the bladder. The following detailed discussion relates to the use of the invention in the treatment of diseases of the prostate. Apparatus dimensions are set forth for embodiments of the apparatus for such treatments. It will be understood by one skilled in the art that appropriate alteration in dimensions of the apparatus may be required to adapt it for the treatment of other conditions, such as in the treatment of tumors of the esophagus and the gastro-intestinal tract based on the particular anatomical dimensions for such other uses.

Figure 1:
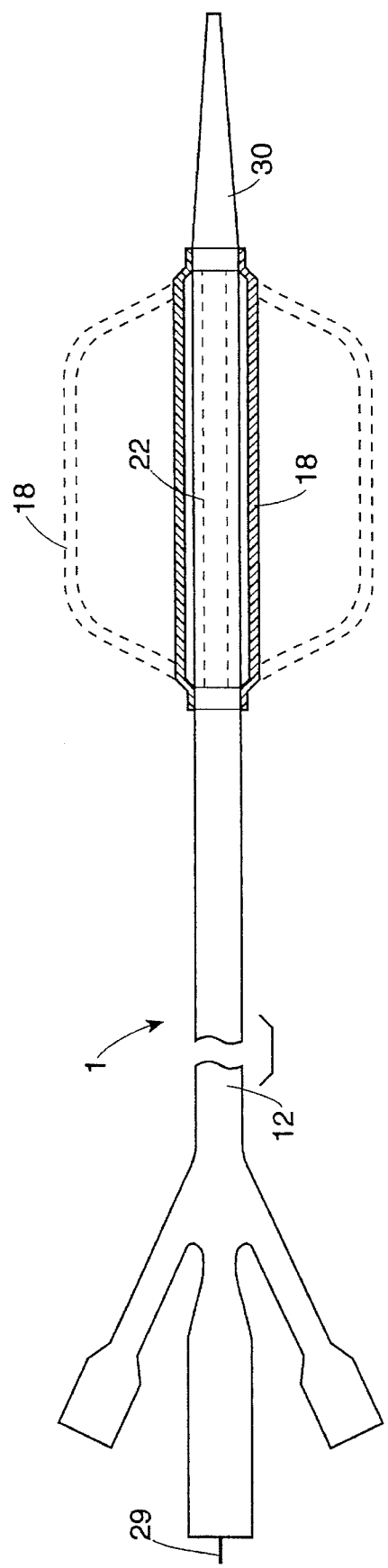
FIG. 1 shows a combined dilation balloon and hyperthermia catheter according to the present invention.

Referring to FIG. 1, a combined dilation balloon and hyperthermia apparatus 1 according to the present invention is illustrated, showing a dilation balloon 18 in deflated position for insertion and withdrawal and in inflated position (shown in dashed lines) for dilation of the prostatic urethra. Heating element 22 at the distal end of outer catheter 12 is also shown.

Figure 2:
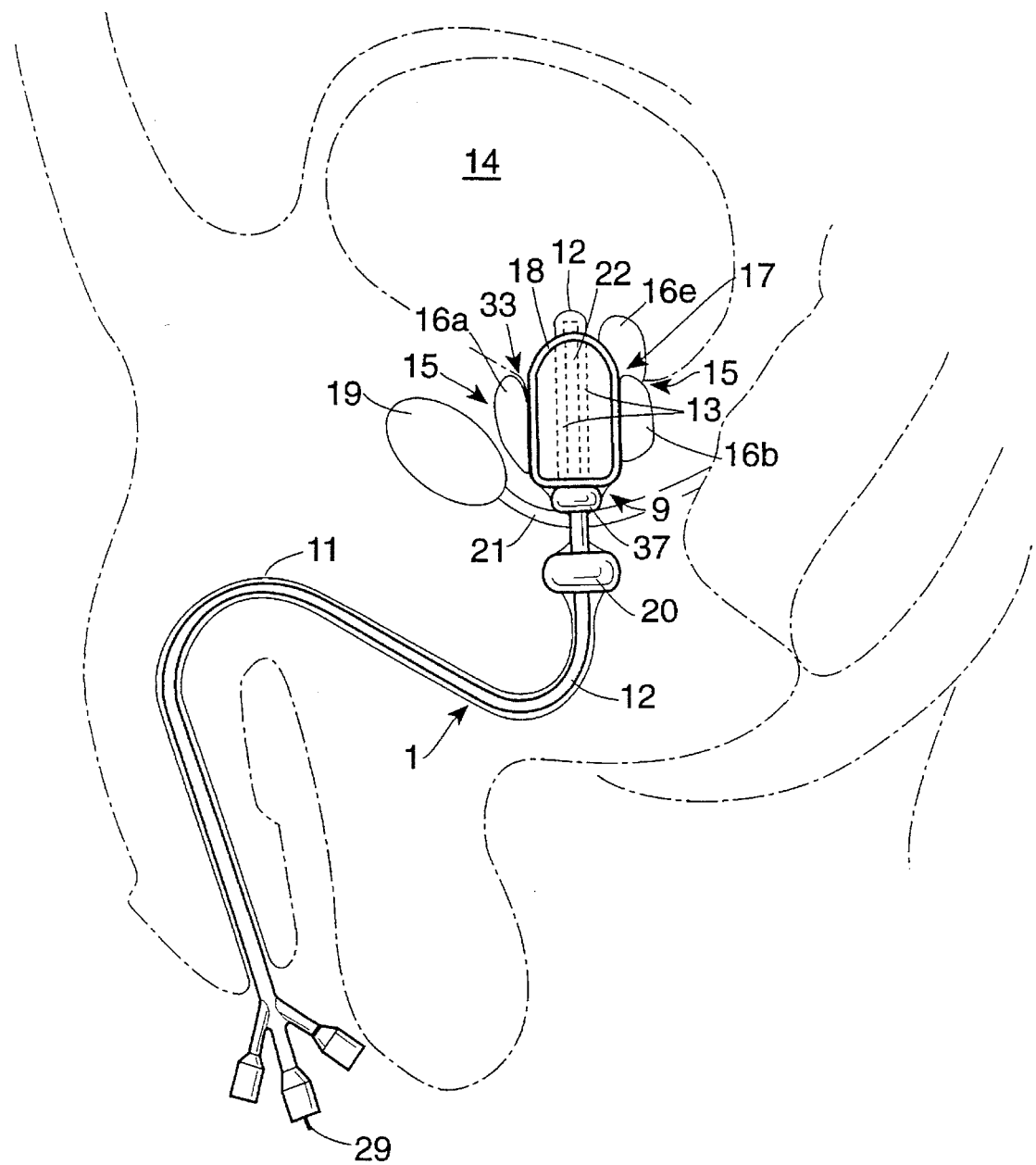
FIG. 2 shows a combined dilation balloon and hyperthermia catheter according to the present invention, also incorporating a fixation balloon, as it is inserted in the male urethra with both fixation balloon and dilation balloon in inflated condition.

Referring to FIG. 2, a combined dilation balloon and hyperthermia apparatus 1, also including a fixation balloon 20, according to the present invention is illustrated, positioned within the male urethra 11. Inflatable fixation balloon 20 is mounted on outer catheter 12 a distance from the distal end thereof such that when the apparatus 1 is properly positioned, fixation balloon 20 is located within the bulbous urethra, proximal to the external sphincter 21. In order to avoid damaging the external sphincter by dilation, protuberance 37 is optionally circumferentially located on outer catheter 12 at a position between fixation balloon 20 and dilation balloon 18 in a direction towards the proximal end of outer catheter 12 to facilitate correct positioning of the apparatus 1 through rectal palpation of the protuberance 37 by the physician. The fixation balloon 20 anchors the apparatus 1 in place and secures it against significant movement in the longitudinal direction. When properly positioned, the distal end of catheter 12 extends slightly past the bladder neck 17 and up into the bladder 14. This enables access of the heating means 22 to the median lobe 16e of the prostate which extends externally past the bladder neck 17 and is adjacent to a portion of the bladder itself. Moreover, in advanced cases of prostate cancer, cancer may spread to the tissue cells of the bladder neck 17 itself, and it is desirable to expose such cells to the hyperthermal treatment as well. Inflatable dilation balloon 18 is mounted on outer catheter 12 at its distal end and when the apparatus I is in place, is properly positioned in the prostatic urethra 9 which passes through the prostate 15. Heating means 22 is axially mounted at the distal end of outer catheter 12 and is situated inside dilation balloon 18. The heating means is a microwave or radio frequency transmitting antenna or a heat-conducting element through which a thermal fluid is circulated to provide heat. In a preferred embodiment of the apparatus, the heating element 22 is a microwave antenna which radiates microwave energy at a frequency of about 915 MHz. In alternative embodiments, shown generally in FIGS. 7a–e, microwave antenna 22 is mounted in an inner catheter member 19 which is independently slidably mounted in outer catheter 12.

Outer catheter 12 is formed of a material which is sufficiently flexible to follow the shape of the urethra upon insertion of the apparatus, while also being sufficiently rigid to enable the apparatus to pass any obstructions in the urethra without bending. Outer catheter 12 is composed of or is covered with a biocompatible material to avoid irritation of the urethra. Suitable materials for outer catheter 12 include polyethylene, silicone, polyester, polyvinylchloride and polyurethane. The preferred material is polyethylene.

Dilation balloon 18 is fabricated such that it does not expand beyond a predetermined diameter. The limited expandability of dilation balloon 18 prevents overdilation and possible damage to the prostatic urethra during dilation. Typically, the dilation balloon 18 is expandable to a diameter of from about 40 French to about 120 French, where the diameter in French is 3.0 times the diameter in millimeters (mm). Therefore, the dilation balloon 18 of the present apparatus ranges in size from about 13 to about 40 mm in diameter.

Dilation balloon 18 and fixation balloon 20 are formed of a biocompatible material, such as polyethylene, silicone elastomer, polyvinylchloride, polyester, polyethylene terphthalate, polyurethane, polyether ether ketone (PEEK), natural or synthetic rubber. The preferred material is polyethylene.

Advantages of the use of polyethylene (PE) over polyethylene terphthalate (PET) are that PE is a softer material than PET and that balloons can be readily fabricated by conventional blowing techniques with accompanying irradiation of the preform material to give it the desired properties of burst pressure and hoop strength.

A balloon preform is made by extruding molten polyethylene on a mandrel having the desired preform (uninflated) dimensions for the balloon. A balloon preform diameter ratio is defined by the expression:

$$\frac{D}{d} = \frac{\text{final balloon diameter}}{\text{preform diameter}}$$

Similarly, a balloon preform length ratio is defined by the expression:

$$\frac{L}{l} = \frac{\text{final balloon length}}{\text{preform length}}$$

The balloon preform diameter ratio relates to the circumferential or hoop strength of the final balloon, while the balloon preform length ratio relates to the axial strength of the final balloon.

A balloon having a preform diameter ratio in the range of from about 4.0–7.0, preferably about 5.9; and a balloon preform length ratio in the range of from about 1.5–3.0, preferably about 2.6, is particularly preferred for either or both the dilation balloon and fixation balloon of a catheter according to the present invention.

Balloons fabricated from polyethylene and having preform diameter and length ratios in the above ranges have been found to have maximal burst pressures in the range of from about 53–68 psi, with an average of about 63 psi; and a hoop strength in the range of from about 9,500–13,300 lbs, with an average of about 11,200 lbs. Balloons fabricated for use as dilation and/or fixation balloons for catheters according to the present invention have a wall thickness in the range of from about 0.0016–0.0024 in., with an average of about 0.002 in.

Figure 3A:
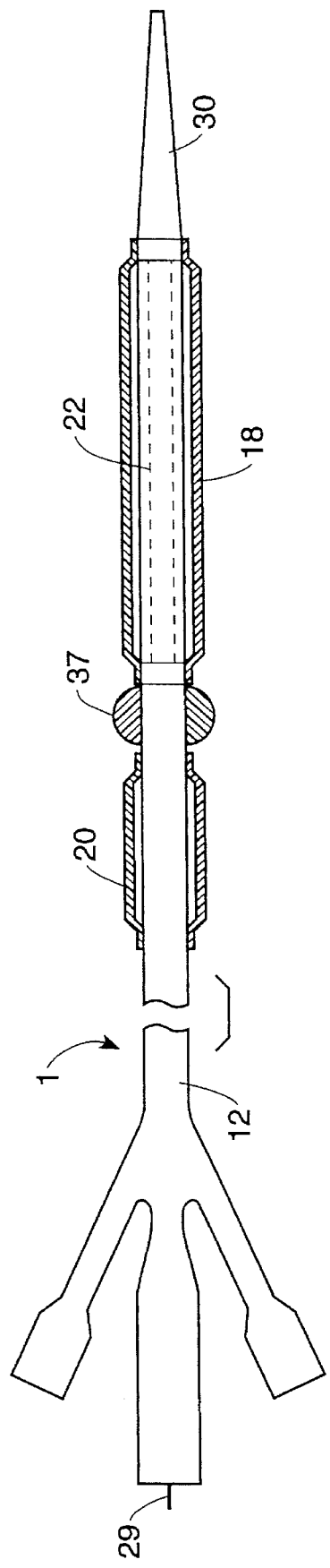
FIG. 3a is a fragmentary sectional view of the apparatus of FIG. 2.

It is possible to fabricate a balloon preform that combines the dilation balloon 18 and fixation balloon 20 in a single-piece unit 5, as shown in FIG. 3b. The extrusion mandrel for forming such a single-piece unit has individual mandrel sections of the desired dimensions connected by a straight section of specified length in between. This results in the formation of a single-piece dual balloon unit with a straight section collar, interspersed between and connecting the two balloons, and having a length corresponding to the straight section length between the mandrel sections on the extrusion die.

Both the dilation balloon 18 and the fixation balloon 20 are attached to outer catheter 12 by bonding thereto. Bonding can be accomplished by use of a biocompatible adhesive, or in the case where both balloons and the outer catheter are fabricated of polyethylene, by heating the material at the point of contact between the balloons and the outer catheter to fuse the balloons to the catheter.

Fixation balloon 20 is located near the distal end of outer catheter 12 but more towards the proximal end of outer catheter 12 than dilation balloon 18. The spacing between fixation balloon 20 and dilation balloon 18 is such that when the entire apparatus is in place, the dilation balloon 18 extends through the bladder neck 17 and into the bladder 14, while the fixation balloon 20 lies to the proximal side of the external sphincter 21. In those embodiments of the apparatus wherein a coolant is circulated in the dilation and fixation balloons, the proximity of the cooled fixation balloon 20 to the external sphincter 21 on its proximal side and to the cooled dilation balloon 20 on its distal side serves to further protect the external sphincter 21 against thermal damage during hyperthermal treatment of the prostate.

Hyperthermia is induced in the target cells by the application of energy to the cells to cause a temperature rise to a therapeutic temperature of at least 42.5° C., for a sufficient time to cause therapeutic changes in the target cells. It has been shown from in vitro tissue studies that the minimum temperature that must be attained in the target tissue cells is 42.5° C. In vivo tests in animals suggest that the optimum temperature to be attained and maintained during hyperthermal treatment in humans is preferably around 48° C. The energy supplied to the tissue cells can be in any form that will effect heating of the tissue. Typically, the energy is electromagnetic radiation energy in the microwave or radio frequency (RF) range, or is thermal conductive energy supplied by circulation of a hot fluid, such as hot water, in the distal end of the apparatus. Microwave energy is the preferred form. The antenna 22 located at the distal end of the apparatus inside of outer catheter 12 and dilation balloon 18 are suitably designed to respectively radiate and selectively transmit electromagnetic energy.

Figure 6:
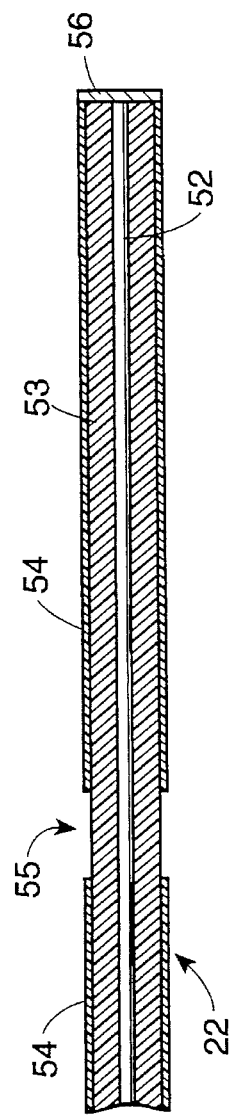
FIG. 6 shows details of a microwave antenna as typically utilized in the apparatus of the present invention.

Microwave antenna 22 is typically a linear coaxial microwave antenna with choke or a standard single junction dipole microwave antenna. The latter is depicted in FIG. 6. The dipole microwave antenna 22 is constructed from a semi-rigid coaxial cable having an inner conductor 52 covered by an insulator 53. The microwave antenna 22 is mounted in antenna lumen 34. The coaxial cable 29 from which the antenna is formed extends from the proximal antenna opening 36 through the length of outer catheter 12 and terminates in the slotted radiating portion of the antenna 22 at the distal end of antenna lumen 34 in outer catheter 12.

In alternative embodiments of the apparatus, the antenna is fixedly attached, slidably mounted or detachably mounted in the antenna lumen 34. The antenna is generally fixed when the overall apparatus is manufactured to be disposable. The antenna is typically slidably mounted where the antenna is of the single junction type with one radiating gap or slot to enable movement of the antenna to direct maximal radiated energy onto various portions of the prostatic tissue along the prostatic urethra. The antenna is detachable where use of a more expensive type of antenna is contemplated and only the catheter tube portion of the apparatus is disposed of after use.

For a single junction dipole antenna 22, an outer conductor 54 is cut circumferentially from the coaxial cable at location 55 to form an axial separation gap of about 0.1 cm between the cut portions of the outer insulator. A metallic connector 56 is soldered between the distal ends of the inner and outer conductors. This simple dipole type antenna operates substantially identically to other dipole style antennae having a soldered connection between the inner conductor and the outer conductor adjacent to the gap. The operation of the dipole microwave antenna 22 as is utilized in the apparatus of the present invention is described more fully in U.S. Pat. No. 4,825,880 to Stauffer et al for Implantable Helical Coil Microwave Antenna, which is incorporated herein by reference.

In one alternative embodiment of the apparatus, utilizing a single junction dipole antenna which is characterized by producing a narrow, mono-nodal peak energy pattern, and due to geometrical considerations in treating an elongated enlarged prostate, the microwave antenna 22 is slidably mounted inside the antenna lumen 34. The apparatus may then be operated in such a way as to enable the antenna 22 to be moved forward and backward within the catheter tube 12 during the catheterization procedure to uniformly expose the prostatic tissue to the maximum amount of energy radiated from a single junction dipole antenna. In this procedure, the position of the antenna can be monitored by ultrasound imaging or by X-ray fluoroscopy.

The exterior surface of outer catheter 12 can be selectively covered with an electromagnetic radiation shielding material. This material may alternatively be a microwave or RF radiation absorbing or reflecting material. The purpose of the shielding material is to control the amount of energy emanating from the outer catheter 12 at any given position along its length and around its periphery. In this way, the strength of the energy field striking any tissue can be varied so that more energy strikes target tissue in thicker regions of the prostate, such as in the transverse lobes 16a, b, while thinner non-target tissue is spared. Where the shielding material is absorptive, the microwave or RF energy is absorbed and dissipated. Where the shielding material is reflective, the microwave or RF energy is reflected inwardly into the outer catheter 12 and is thus prevented from escaping to strike tissue. The selective use of electromagnetic shielding material to attenuate field strength in selected directions enables the fabrication of various embodiments of the apparatus, each having a unique energy emission profile, suitable for use in a particular situation based on considerations of individual patient anatomy, including size and thickness of the prostate, and nature and extent of the disease. The shielding material can be applied to cover the full length of outer catheter 12, from its proximal end to its distal end, except for the section adjacent to the dilation balloon where it is desired to have the unattenuated microwave or RF energy emitted, in order to protect the bladder wall and external sphincter, respectively, from unnecessary exposure to potentially damaging microwave or RF radiation. A choked-end antenna can also be used as a microwave antenna 22 to limit the microwave energy field directed toward the proximal end of the apparatus.

The electromagnetic energy shielding material can also be applied to selected portions of the outer surface of dilation balloon 18 either alternatively to or in addition to its application to selected regions of the outer catheter 12. The material can be sputter-coated onto the balloon surface.

Any electromagnetic energy absorbing or reflective material can be utilized for the catheter shielding material. It has been found that teflon is an especially effective and preferred material.

FIG. 8 shows a shielded apparatus according to the present invention. FIGS. 9a–b show patterns of microwave energy irradiation in the prostate gland for a shielded and a partially shielded apparatus, respectively.

At the distal end of combined microwave hyperthermia and dilation apparatus 1, shown in FIG. 8, microwave antenna 22 radiates microwave energy 30 which passes through wall 13 of outer catheter 12 and dilation balloon 18. Outer catheter 12 and dilation balloon 18 are fabricated from material having a low dielectric constant which has a high transmittance and low absorbance of microwave energy, such as polyethylene. Microwave antenna 22 ordinarily radiates energy radially outwardly in a 360° field perpendicular to its longitudinal axis, as well as radiating reflected microwave energy both in a forward direction 45 and a rearward direction 47 along the longitudinal axis of the antenna. In order to effectively direct microwave energy 30 to selected target diseased prostatic tissue and avoid undesirable effects of heating non-diseased prostatic tissue and surrounding tissue such as that of the urothelium to avoid damage to such tissue, and to avoid dissipation of microwave energy from the desired target tissue into undesired areas, which also requires the expenditure of a greater amount of power and provision of a larger power source, microwave antenna 22 itself can also be provided with an insulation sheath 65 along most of its length, to concentrate the emission of microwave energy in a point source at the exposed portion 64 of the antenna length. A shield 62, made of a microwave absorbing or reflective material, is applied to selected portions of the outer surface of outer catheter 12. The absorptive material has a high dielectric constant and thermally collects energy without dissipating heat into tissue. Alternatively, a material which is only partially microwave energy absorbant can be used to attenuate but not completely eliminate the microwave energy field emanating in a particular direction. Where reflective material is used, the microwave energy is internally reflected and does not radiate through the outer catheter at those points which are shielded. Thus, where the target diseased prostate tissue is confined to the two lateral lobes of the prostate, completely microwave absorbant shielding material may be utilized to limit and direct microwave radiation emission from the catheter laterally into the lobes. Where the diseased prostatic tissue has spread, however, it may be desired to only partially shield the catheter in other directions around its periphery so that at least a reduced energy field is emanated in those other directions. The thickness of the shielding can be varied to generally account for variation in the thickness of the prostate and thinner non-prostate tissue so that the emergent radiation in a particular direction is proportional to the thickness of the prostate gland or thinness of other tissue in that particular direction. This enables an appropriate amount of microwave energy to be directed toward a specific point, so that maximum possible therapeutic treatment of diseased prostate, and if also necessary, bladder neck tissue, occurs while damage to non-diseased prostatic tissue and surrounding tissue is avoided.

FIG. 9a shows outer catheter 12 deployed in the prostatic urethra 9, with dilation balloon 18 inflated and with the outer surface of outer catheter 12 covered with a totally shielding material 57 around a portion of its periphery to restrict emanation of microwave energy laterally along lines 30 to arcuate segments 70–71 and 72–73 and into the two lateral lobes 16a, b of prostate 15 and not in other parts 16c,d of the prostate.

FIG. 9b shows outer catheter 12 deployed in the prostatic urethra 9, with dilation balloon 18 inflated and with the outer surface of outer catheter 12 covered with only a partially microwave absorbing shielding material 57' around a portion of its periphery to allow a reduced microwave energy field to radiate into those parts of the prostate 16c,d above and below the lateral lobes 16a, b. The reduced strength fields are shown by arcuate sections 74–75 and 76–77.

In alternative embodiments of the apparatus, outer catheter 12 has a plurality of from 2 to 10 lumens and channels for various features.

Figure 4A:
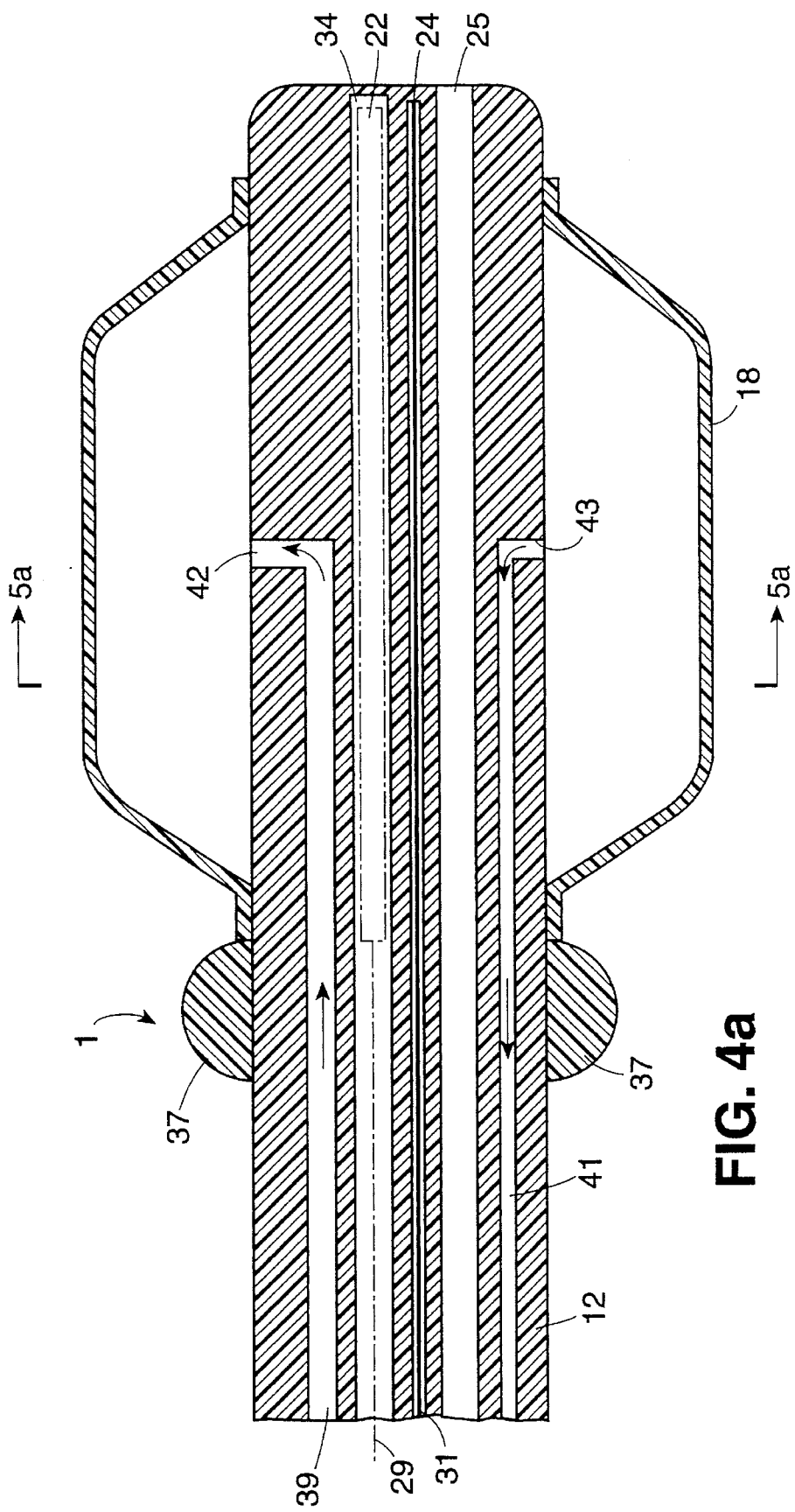
FIG. 4a is a cross-sectional view of the distal end of the device of FIG. 3 showing the dilation balloon in inflated condition.
Figure 4B:
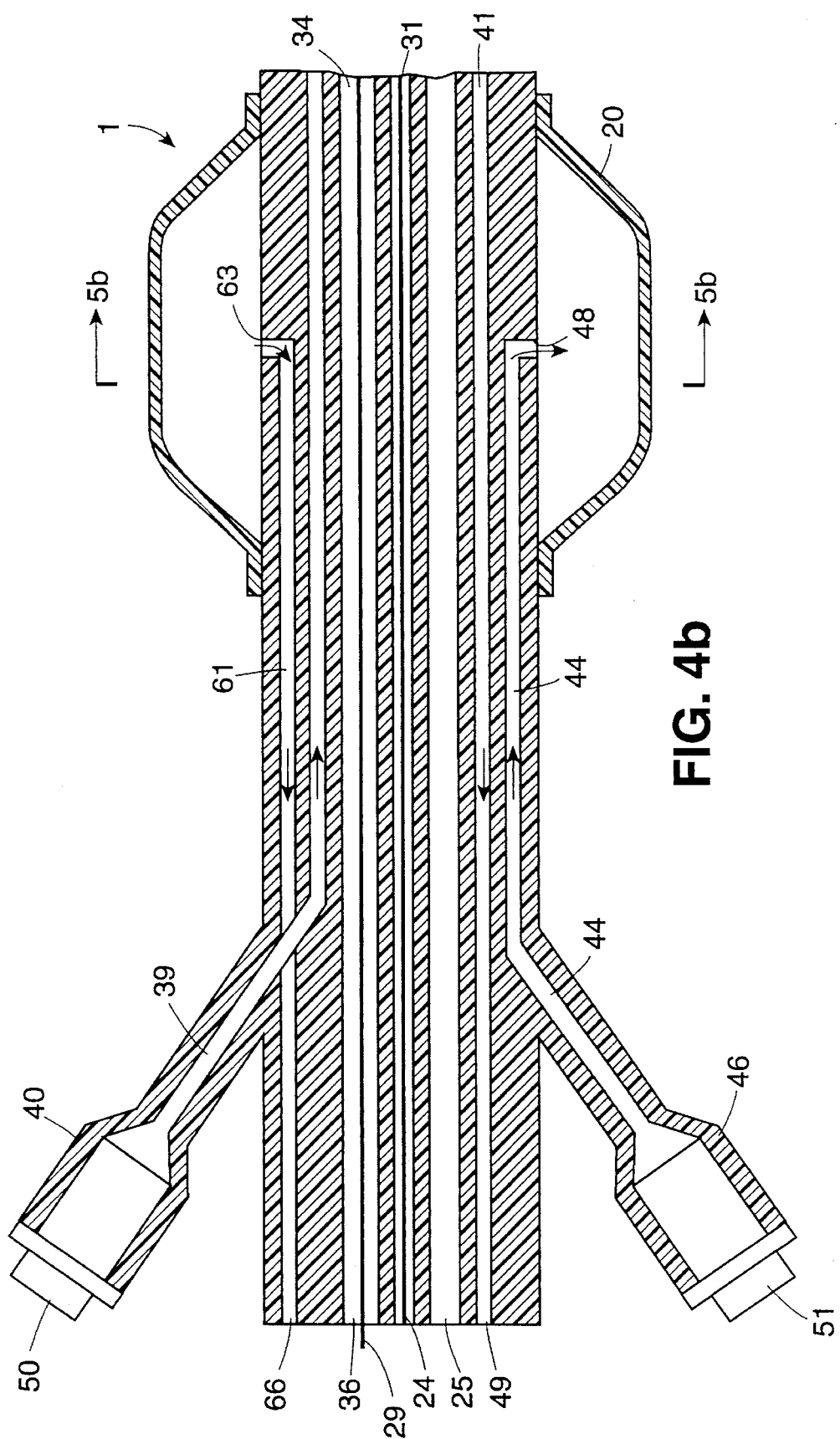
FIG. 4b is a cross-sectional view of the proximal end of the device of FIG. 3 showing the fixation balloon in inflated condition.
Figure 5A:
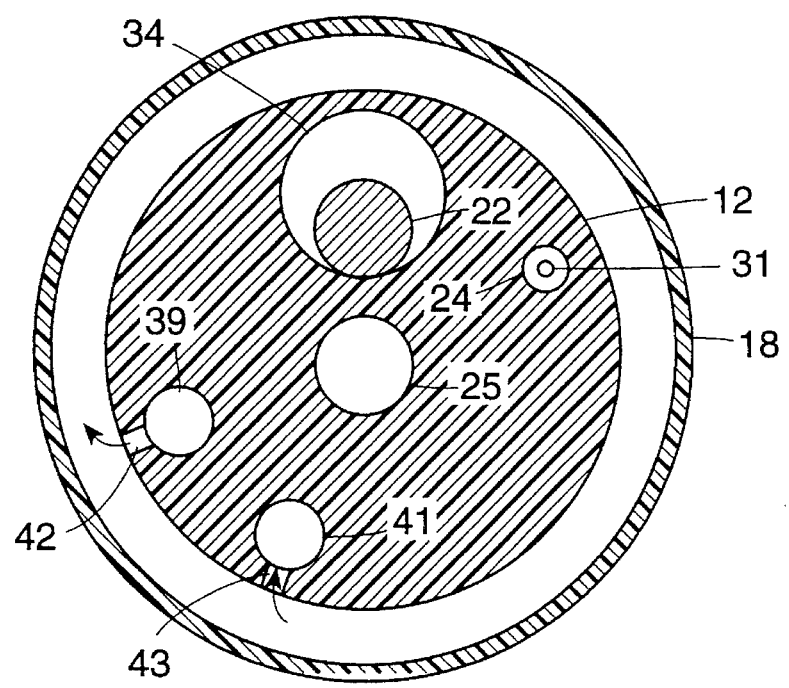
Figure 5B:
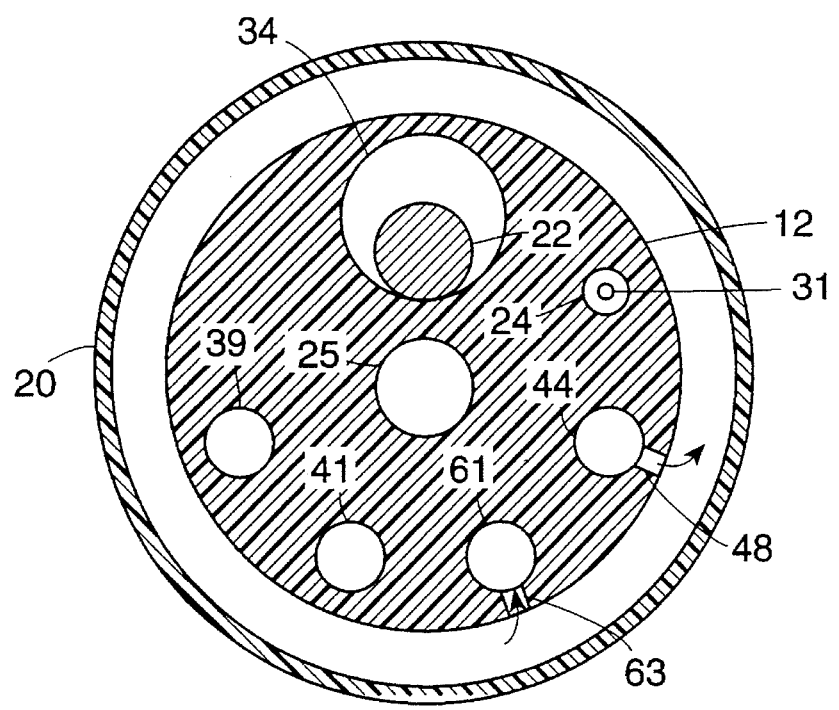
FIG. 5b is a cross-sectional end view of the apparatus through location 5b—Sb of FIG. 4b.
Figure 5C:
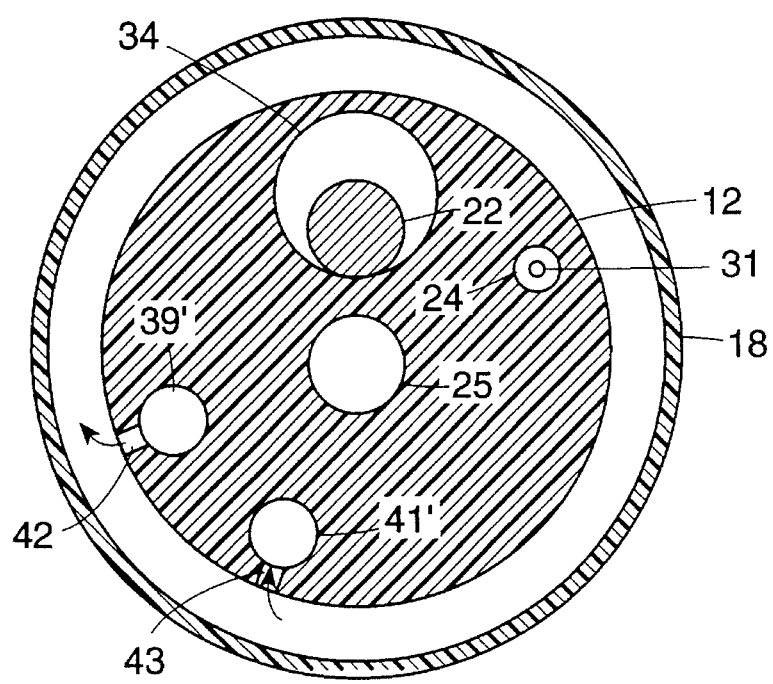
FIG. 5c is a cross-sectional end view of the apparatus through location 5c—5c of FIG. 4e.
Figure 5D:
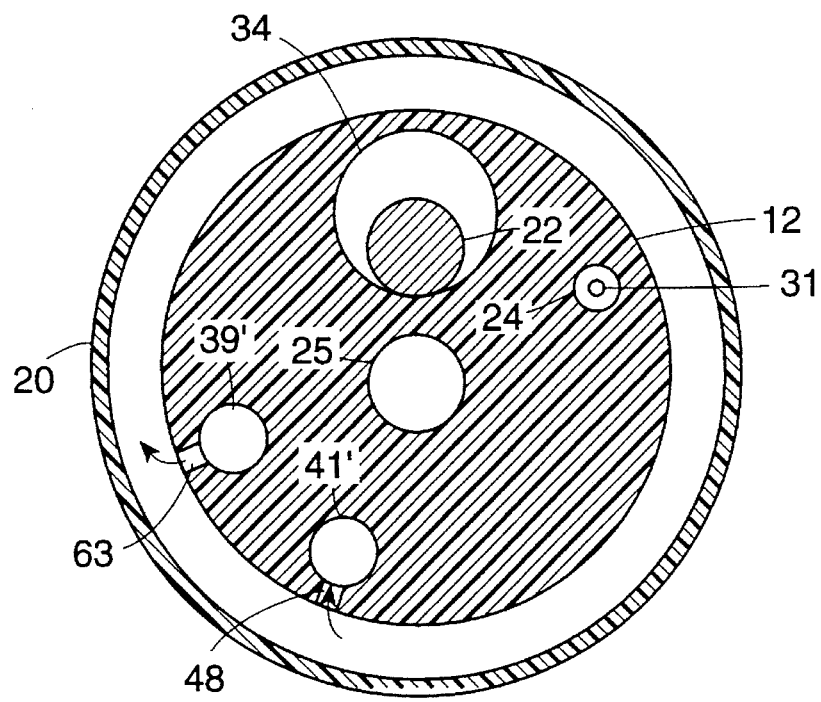
FIG. 5d is a cross-sectional end view of the apparatus through location 5d—5d of FIG. 4f.
Figure 5E:
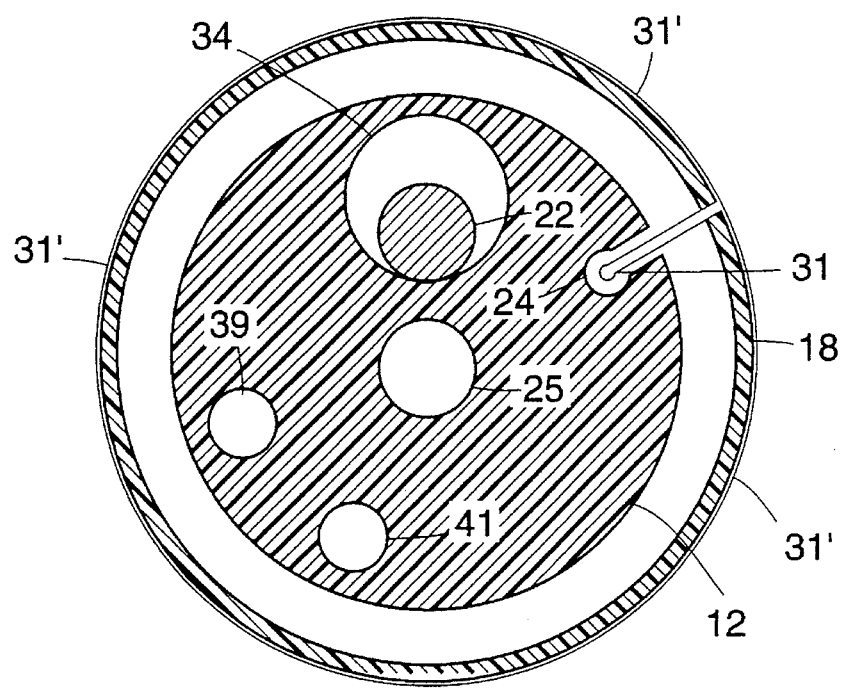
FIG. 5e is a cross-sectional end view of the apparatus through location 5e—5e of FIG. 4g.
Figure 5F:
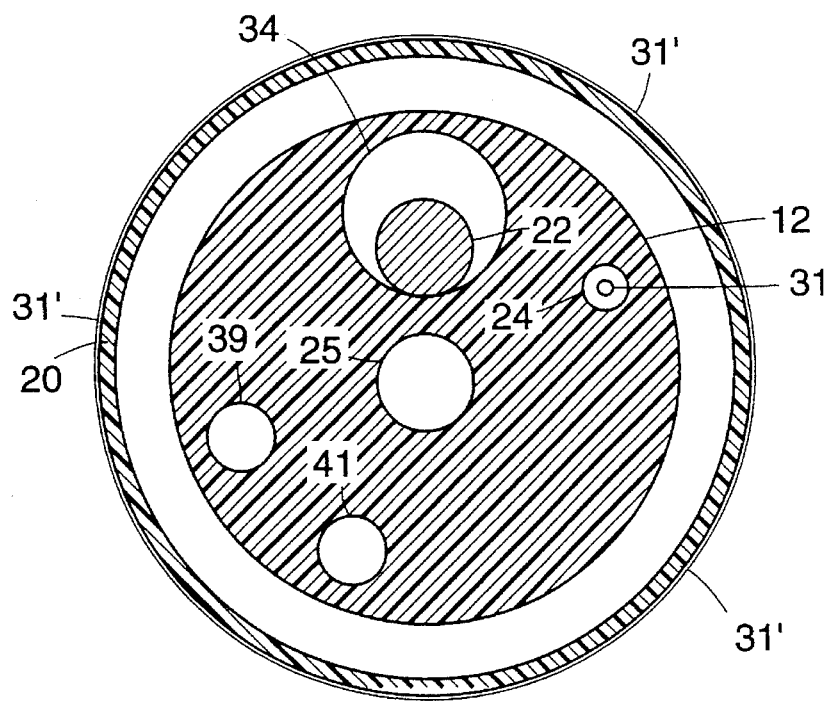
FIG. 5f is a cross-sectional end view of the apparatus through location 5f—5f of FIG. 4g.

FIGS. 5a and 5b are cross-sectional views of the apparatus 1 at locations 5a—5a and 5b—5b, respectively, of outer catheter 12, as shown in FIGS. 4a and 4b.

Referring to FIGS. 4a, 4b, 5a, and 5b, antenna lumen 34 extends from the distal end of outer catheter 12 through the catheter to the proximal end where it terminates in proximal antenna opening 36. Dilation lumen 39 communicates between dilation balloon inflation port 40 and dilation balloon 18, via dilation balloon opening 42. FIGS. 4a, 4b, 5a and 5b additionally show other lumens in a preferred embodiment of the apparatus. Fixation lumen 44 communicates between fixation balloon inflation port 46 and fixation balloon 20 via fixation balloon opening 48.

One alternative embodiment of the apparatus includes a plurality of more than two ports and connectors for other lumens, such as for the inflation cooling outflow, thermometry means, and antenna. The ports may be arranged in a manifold. Dilation balloon inflation port 40 and fixation balloon inflation port 46 are each provided with a valve or a syringe fitting 50 and 51, respectively, to allow for connection of the fill ports with syringes or other means for injection or circulation of inflation/cooling fluid. Dilation drainage lumen 41 communicates between dilation balloon 18, via dilation balloon outlet 43 to dilation outlet port 49. Fixation drainage lumen 61 communicates between fixation balloon 20, via fixation balloon outlet 63 to fixation outlet port 66. In an alternative embodiment, where the inflation/cooling fluid circulated in both the fixation balloon 20 and the dilation balloon 18 is the same, dilation lumen 39 and fixation lumen 44, and dilation drainage lumen 41 and fixation drainage lumen 61, are combinable into single inflation and drainage lumens, respectively.

In certain embodiments, thermometry lumen 24 accommodates thermometry means used to monitor the temperature of the urethral wall. This lumen also extends the full length of outer catheter 12. In such embodiments, temperature sensing means 31 is housed in thermometry lumen 24. The temperature sensing means is a thermocouple, a thermister or a fiber-optic temperature sensor. The distal end of temperature sensing means 31 measures the temperature of the dilation balloon inflation/coolant fluid which at equilibrium is a measure of the urethral wall temperature. From appropriate correlations, the actual temperature attained in the diseased prostate tissue is determinable. According to one embodiment, when the temperature sensing means 31 is a thermocouple, it is constructed to have a heat-conducting metallic element 31 attached to and covering at least a portion of the outer surface area of dilation balloon 18 when the balloon is inflated, as shown in FIG. 4g. The metallic element can be attached to the balloon by sputter-coating or by bonding to the balloon. In one alternative embodiment, the temperature sensing means 31 is placed in the coolant outlet port to measure the coolant outlet temperature which is essentially the same as the urethral wall temperature at equilibrium. In another alternative embodiment, temperature sensing means 31 is carried externally on outer catheter 12 and, in such embodiment, an internal thermometry lumen 24 is not required. In still other embodiments, a separate rectal temperature probe can be used to monitor rectal wall temperature which can be correlated to temperature attained in the prostate; or an interstitial temperature probe can be inserted into the prostate to directly measure prostate temperature during hyperthermal treatment.

The apparatus may also include means for regulating the amount of energy provided to the antenna 22, such as by the use of a feedback circuit to control tissue temperature within a preset range.

Drainage lumen 25 allows urine to drain from the bladder 14 while the apparatus is in position. Drainage lumen 25 extends from the distal end of the outer catheter 12, which extends through the bladder neck 17 and into the bladder 14, all the way through to the proximal end of the outer catheter 12. Drainage of urine and fluids can be passive or suction means can be used.

Lumens and channels in outer catheter 12 are configurable in a number of alternative ways, such as are described by the following, non-limiting additional examples. All of these alternative configurations generally include an inner catheter member 19 which itself contains one or more lumens and which serves to create one or more channels between itself and the inner wall of outer catheter 12. Inner catheter member 19 can be made to be either independently slidable and/or rotatable with respect to outer catheter 12 or fixed with respect thereto. Inner catheter member 19 is fabricated from a material which is alternatively the same material as or is different from the material used for outer catheter 12, and is preferably made of polyethylene.

Figure 7A:
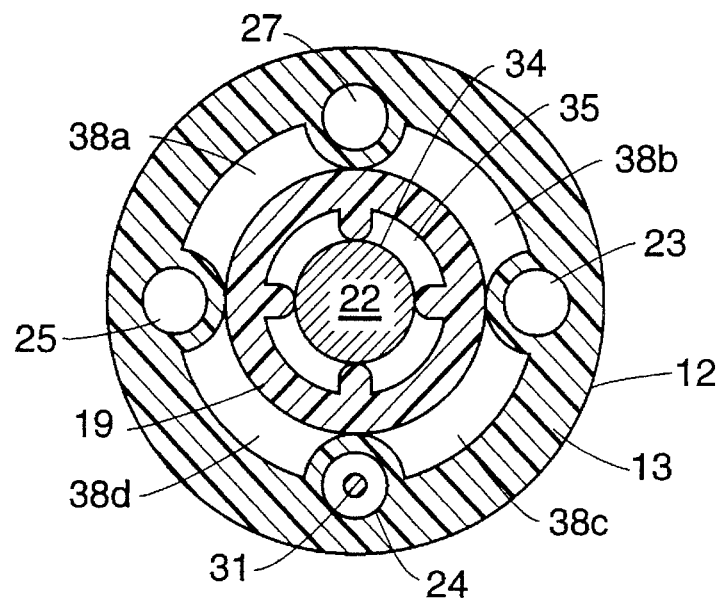

In one preferred embodiment, shown in FIG. 7a, antenna lumen 34 is centrally located in outer catheter 12. Microwave antenna 22 fills the central core of antenna lumen 34. Antenna lumen 34 is surrounded by antenna coolant inlet lumen 35 through which a coolant is circulated to cool the microwave antenna 22 and prevent its overheating. The interior of outer catheter 12 is segmented into a second major concentric compartment by the provision of inner catheter member 19, which surrounds central antenna lumen 34 and antenna coolant inlet lumen 35. Warmed coolant is withdrawn through antenna coolant outlet lumen 38. Antenna coolant inlet lumen 35 and antenna coolant outlet lumen 38 communicate with each other at the distal end of outer catheter 12. The arrangement of antenna coolant lumens 35 and 38 provides a concentric flow pattern of coolant around microwave antenna 22.

Figure 7B:
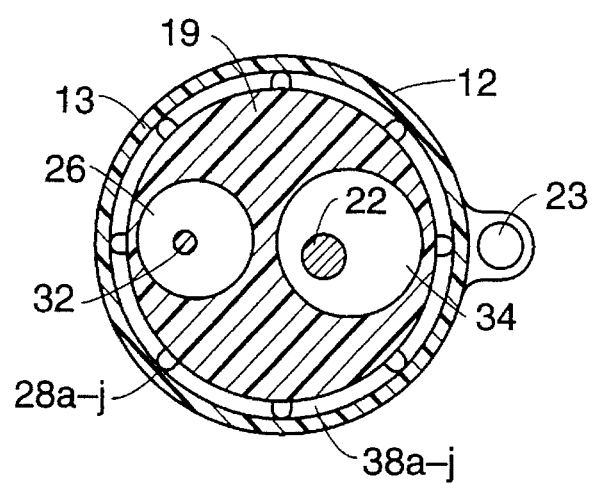

In this embodiment, other lumens are provided around the antenna lumen 34 and antenna coolant lumens 35 and 38, situated outwardly toward the periphery of outer catheter 12. These additional lumens are configurable in a number of ways. According to one embodiment, the peripherally located lumens include fixation balloon lumen 23, thermocouple lumen 24, and drain 25. Additional lumens can be situated around the periphery as required, such as extra lumen 27, shown in phantom. Where the required lumen is wider than can be accommodated by the wall thickness of outer catheter 12, the wall portion can be thickened by providing a "hump" which protrudes from the outer cylindrical surface of outer catheter 12. FIG. 7e illustrates an identical configuration to that of FIG. 7a, however, because a larger diameter lumen is required for guidewire 32 than can be accommodated in extra lumen 27 of FIG. 7a, a "hump" is provided in the outer wall of outer catheter 12 to accommodate guidewire lumen 26.

In another alternative embodiment, shown in FIG. 7b, cylindrical outer catheter 12 includes two major multi-functional internal lumens, an antenna lumen 34 which is sufficiently large to also enable inlet circulation of coolant around antenna 22 in the same lumen, and guidewire lumen 26 through which a guidewire 32 is passed when the catheter is positioned and is then withdrawn after the catheter is fixed in place, with the lumen subsequently functioning as a drain for removal of fluids. Withdrawal of antenna coolant is through annular antenna coolant outlet lumens 38a–j near the outer periphery of outer catheter 12 formed by inner catheter member 19. Guidewire lumen 26 and antenna lumen 34 are formed by boring these lumens through solid inner catheter member 19. Inner catheter member 19 is a solid cylindrical tube having an outer diameter smaller than the inside diameter of outer catheter 12. Inner catheter member 19 has a plurality of flanges or raised ridges 28 extending longitudinally along its length. Viewed in plane view, these flanges appear as a series of humps on the outer periphery of inner catheter member 19. The number of flanges 28 is typically from 4 to 10, with 10 being shown in FIG. 7b (28a–j). The height of the flanges 28 corresponds to the distance between the outer diameter of inner catheter member 19 and the inner diameter of outer catheter 12. The flanges 28 create a plurality of channels 38 (10 being shown in FIG. 7b, 38a–j) which function as the above-mentioned antenna coolant outlet lumens. The flanges 28 can also serve to hold inner catheter member 19 in place with respect to outer catheter 12. This is accomplished by providing means on the inner surface of outer catheter 12 with which the flanges 28 cooperatively engage to prevent both longitudinal and rotational movement of inner catheter member 19 in outer catheter 12. Alternatively, inner catheter member 19 can be made to be independently slidable inside outer catheter 12. Fixation balloon lumen 23 is provided in an external "hump" which is appended to the outer periphery of cylindrical outer catheter 12.

Figure 7C:
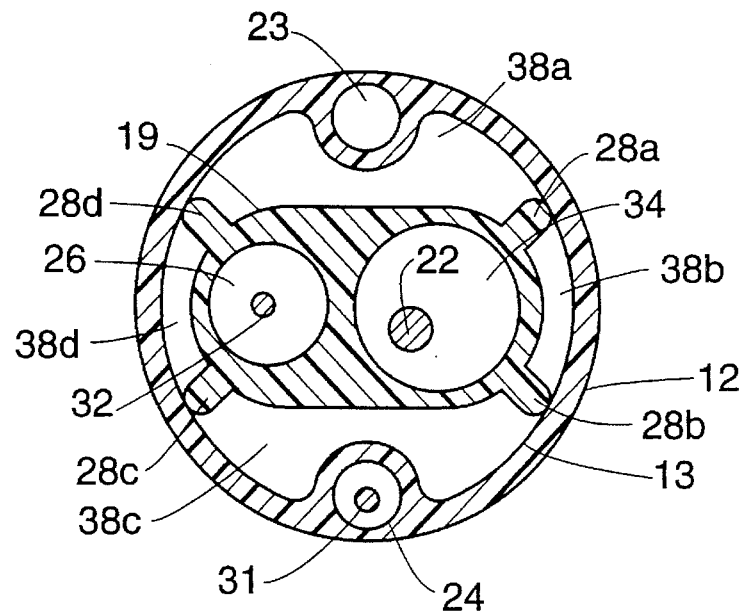

In a still further embodiment, the interior space of outer catheter 12 contains a number of lumens and channels as is shown in FIG. 7c. Inner catheter member 19 has a generally elongated oval shape, which in plane view gives the appearance of having been formed by drawing apart semi-circular halves to form a straight sided segment between the halves, and further has a flange 28a–d at each of four locations, two on each semi-circular end. When viewed in plane view, these flanges divide the interior space of outer catheter 12 into four arcuate channel segments around the periphery of the inner wall of outer catheter 12. These flanges attach inner catheter member 19 to the inner surface of outer catheter 12 and divide the annular space formed between inner catheter member 19 and outer catheter 12 into the arcuate channel segments. These four segments function as antenna coolant outlet lumens 38a–d. Inner catheter member 19 is itself provided with two cylindrical lumens disposed therein adjacent to one another. Both of these two cylindrical lumens are multi-functional lumens, one being a guidewire lumen 26, through which guidewire 32 is passed also functions as a drain; and the other being an antenna lumen 24, having antenna 22 disposed therein, and which also functions as an antenna coolant inlet lumen. Other lumens, such as fixation balloon lumen 23 and thermocouple lumen 24 are situated in a thickened portion of the wall 13 of outer catheter 12 at points around its periphery, typically opposite the straight sided portion of inner catheter member 19. The outer catheter wall has a typical wall thickness of from 0.007 to about 0.010 in. Depending on the overall configuration of lumens and channels, the wall thickness of wall 13 of outer catheter 12 can be inwardly increased at selected points around its cylindrical periphery to accommodate the bores of smaller lumens without the need for disrupting the generally cylindrical shape of outer catheter 12. Larger diameter lumens than cannot be bored through a thickened section of wall 13 of outer catheter 12 are provided by creating a hump or bulge which protrudes beyond the cylindrical periphery of outer catheter 12.

Figure 7D:
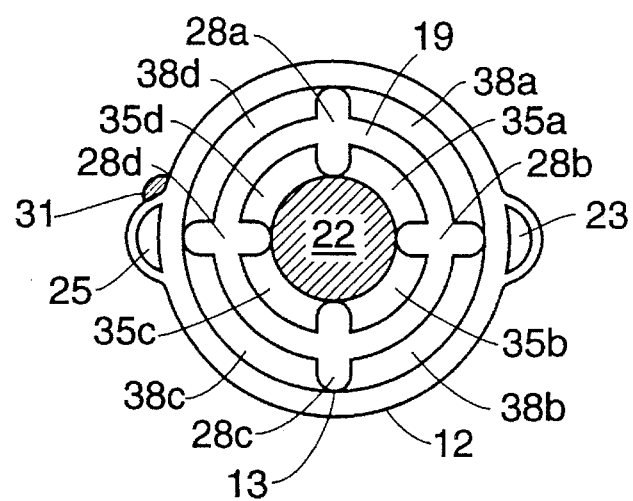
Figure 7E:
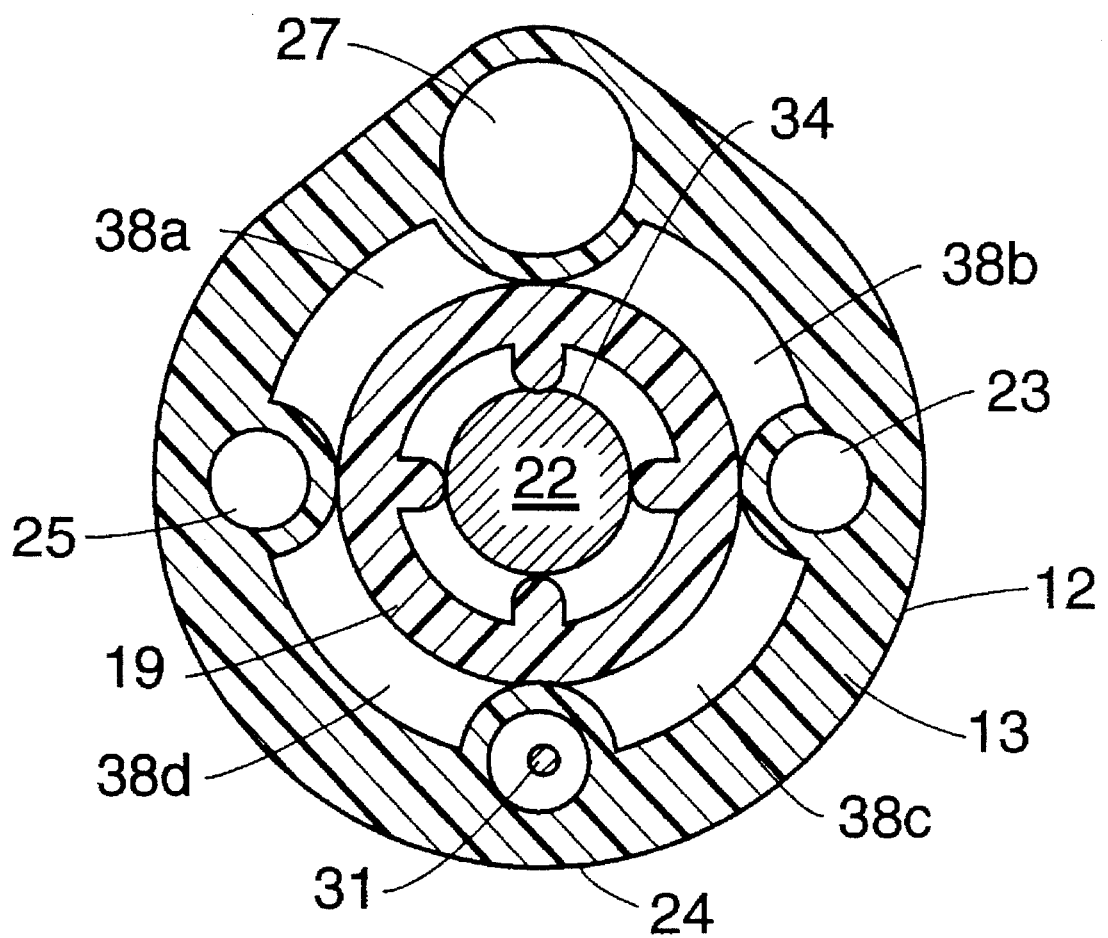

FIG. 7d illustrates yet another alternative embodiment of internal configuration of outer catheter 12. The interior space of outer catheter 12 is divided into a number of arcuate channel segments by ring-like inner catheter member 19, as in FIG. 7c, however, inner catheter member 19 is here substantially circular rather than oval. Four flanges 28a–d disposed approximately equidistantly around the outer periphery of inner catheter member 19 extend outwardly to attach inner catheter member 19 to the inner surface of outer catheter 12 and divide the annular space formed therebetween into four arcuate channel segments. These arcuate channel segments serve as antenna coolant outlet lumens 38a–d. The flanges 28a–d also extend inwardly to serve as centering posts for microwave antenna 22 which is centrally disposed within the inner space of ring-like inner catheter member 19. The inner diameter of ring-like inner catheter member 19 is larger than the outer diameter of microwave antenna 22 such that an annular space is formed between inner catheter member 19 and antenna 22. This annular space is segmented by inwardly extending flanges 28a–d to form four arcuate channel segments which function as antenna coolant inlet lumens 35a–d. Additional lumens are disposed around the outer periphery of cylindrical outer catheter 12, in "humps" on the outer surface thereof. These humps are sections of increased thickness of the wall 13 of outer catheter 12 through which the lumens or channels pass. Where provision for more than one such additional lumen is required, the humps are generally disposed equidistantly around the periphery of outer catheter 12. Shown in FIG. 7d are fixation balloon lumen 23 and drain 25. In this particular embodiment, thermocouple 31 is attached to the exterior surface of outer catheter 12 and runs longitudinally along the length of outer catheter 12 instead of being disposed in a separate internal thermocouple lumen. FIGS. 5a, b and 7b, c also serve to illustrate embodiments wherein the inner catheter member and heating means lumen are asymmetrically situated. In this manner, the strength of the energy field emanating from the catheter in a particular orientation can be controlled. Since the material of the inner catheter and outer catheter is energy absorbant, the field emanating will be stronger in the direction where the lumen and antenna is closer to the outer wall and weaker in the direction further from the outer wall.

Inner catheter member 19 functions to center microwave antenna 22 inside outer catheter 21 so that a symmetrical microwave energy field is provided to tissue being irradiated, and the chance of damage to the rectal wall and the external sphincter is minimized.

Each lumen or channel shown in FIGS. 7a–e generally extends the entire length of outer catheter 12 and communicates with a corresponding appropriate inlet or outlet port at the proximal end of outer catheter 12. For example, referring to FIGS. 4a–b, drainage lumen 25 communicates with a port to which a source of suction can be connected to remove urine and other fluids during the procedure.

Figure 4C:
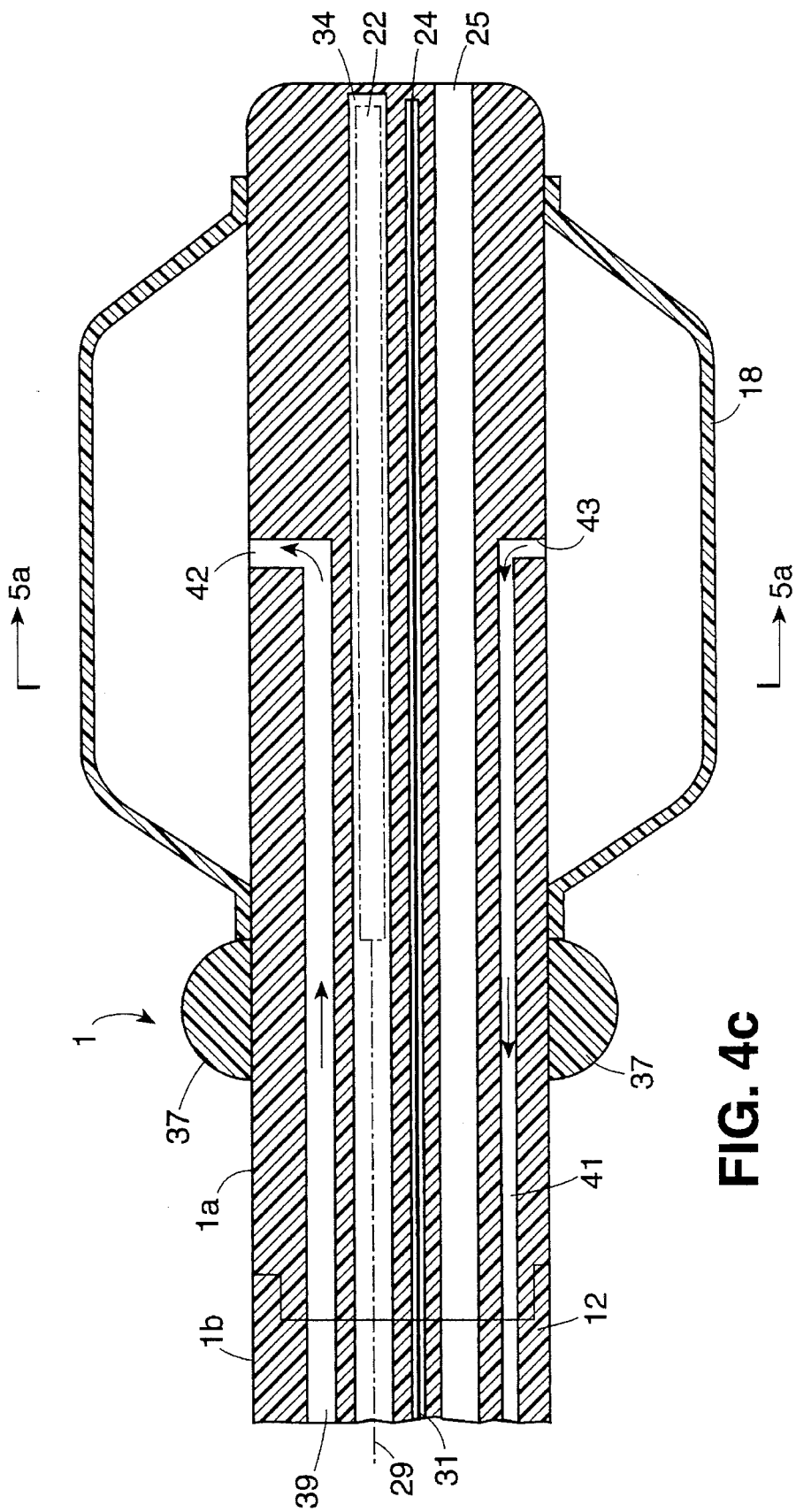
FIG. 4c is a cross-sectional view of the distal end of an embodiment of the device according to the present invention, having a plurality of interconnecting subsections.
Figure 4D:
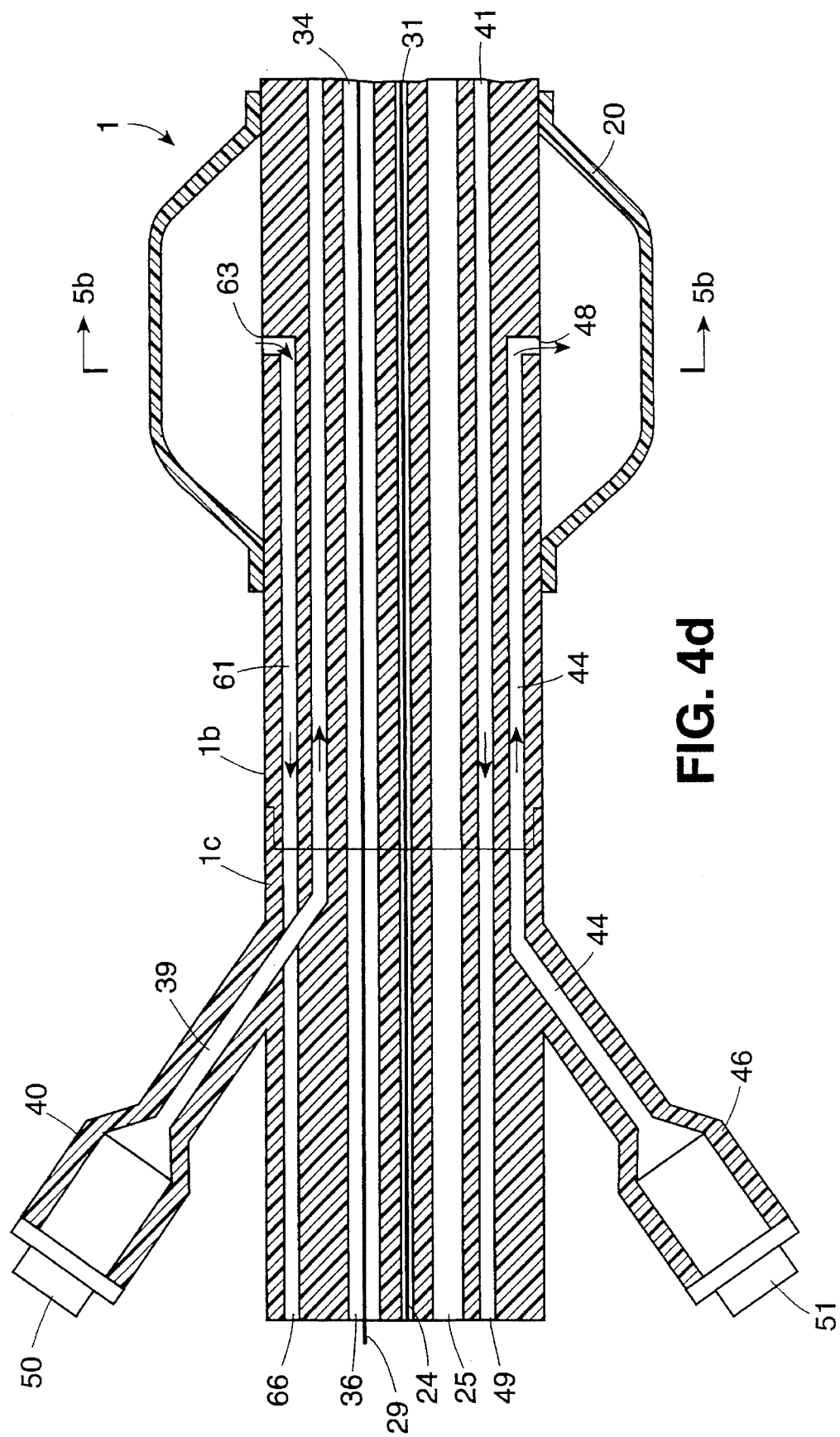
FIG. 4d is a cross-sectional view of the proximal end of an embodiment of the device according to the present invention, having a plurality of interconnecting subsections.

In order to make assembly of catheters according to the present invention convenient and economical, outer catheter 12 can be fabricated in several interconnectable, disposable pieces. By doing this, assembly is made easier and overall costs are minimized since it is easier to mold the outer catheter 12 in several smaller sections than as one large piece because less complicated extrusion equipment is needed for smaller sections than for one large piece. Moreover, by making the outer catheter 12 separate and detachable from the internal elements, especially the microwave antenna 22, those more costly elements of the apparatus can be saved and re-used. Only that part of the apparatus, outer catheter 12, which comes into direct contact with the patient, is discarded and replaced to ready the apparatus for re-use. In this way, moreover, time consuming and costly re-sterilization of the entire apparatus is avoided FIGS. 4c–d show one preferred embodiment of a catheter according to the present invention, having a plurality of interconnectable subsections, with three such subsections 1a, 1b and 1c being shown.

Typically, outer catheter 12 is fabricated in two or three interlocking sections. Where three sections are used, they are typically a manifold section which includes the ports at the proximal end of the apparatus, a catheter stock section which includes the mid-section of the outer catheter, and a balloon section which includes the dilation and fixation balloon deployment sections of the catheter.

A further advantage of this modular type construction is that the internal configuration of lumens and channels through each piece can be varied and customized to optimize its performance. This is accomplished by fabricating each separate section in such a way that a section has a common configuration of lumens and channels with the next adjacent section to which it is to be attached. Throughout each given section, however, the configuration of lumens and channels can be varied. The cross-sectional arrangement of lumens along the axial length of a first sub-section is the same as or different from the cross-sectional arrangement of lumens along the axial length of other sub-sections immediately adjoining the first sub-section at either end. Lumens in the first sub-section cooperate with functionally corresponding lumens in adjoining sub-sections by means of transition zones at both the proximal and distal ends of a sub-section, wherein the cross-sectional arrangement of lumens is identical to the cross-sectional arrangement of lumens in the transition zones of the other sub-sections with which the first sub-section is interconnected at either end. For example, it may be desired to have a plurality of coolant fluid conducting lumens disposed around the periphery of the outer catheter in the section disposed nearest to the rectal wall and external sphincter when the catheter is fixed in place to provide additional cooling to prevent damage to these tissues.

The fixation and dilation balloons are capable of being inflated to a predetermined size by the injection of corresponding volumes of inflation fluid into each, which is supplied through their respective inflation lumens or through a common inflation lumen in the case where the apparatus is so adapted to utilize a single common inflation fluid supplied through a single lumen. The corresponding drainage lumen or lumens are closed by closing the respective outlet port(s) and the fluid is injected to inflate the balloons. The inlet port(s) are then closed to maintain the fluid inside the balloons.

Figure 4E:
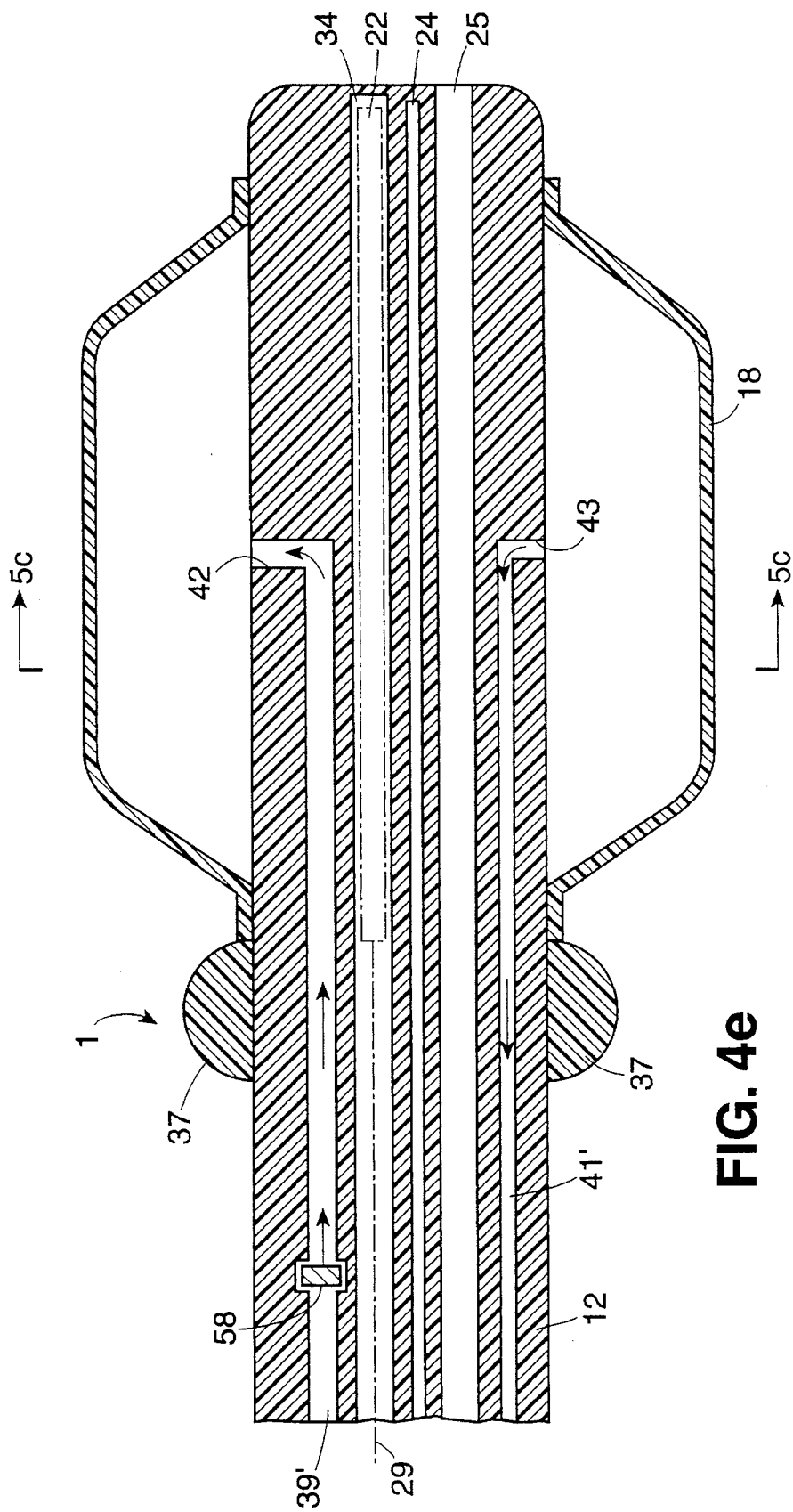
FIG. 4e is a cross-sectional view of the distal end of an embodiment of the device according to the present invention, having a single inlet port and lumen and a single outlet port and lumen, each in communication with both the dilation balloon and the fixation balloon.
Figure 4F:
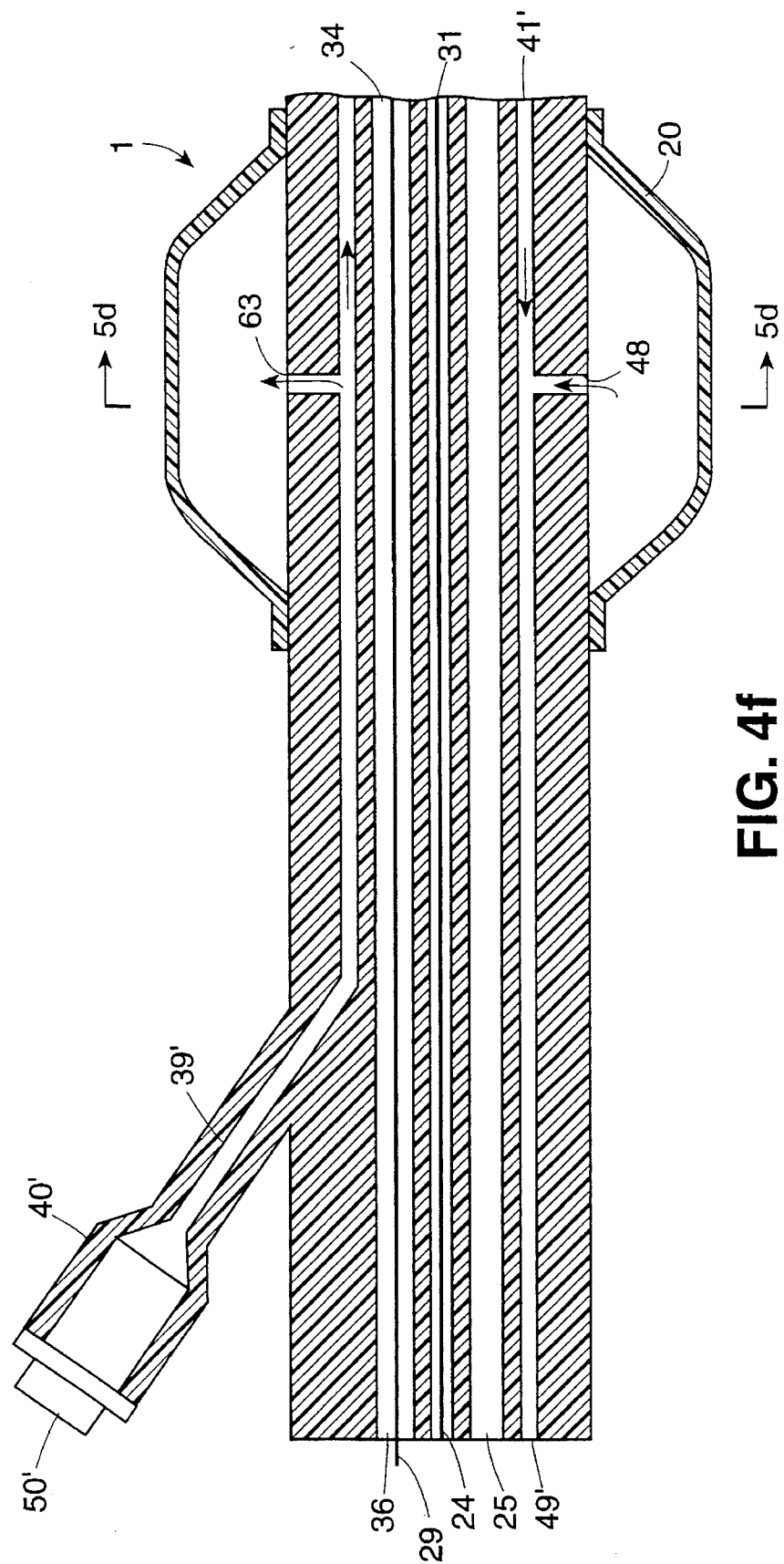
FIG. 4f is a cross-sectional view of the proximal end of an embodiment of the device according to the present invention, having a single inlet port and lumen, and a single outlet port and lumen, each in communication with both the dilation balloon and the fixation balloon.

One embodiment of apparatus according to the invention shown in FIGS. 4e–f, includes a single inlet lumen 39' which communicates with both the dilation balloon 18 and the fixation balloon 20 and an inlet port 40' at the proximal end of the outer catheter; and further has a single outlet lumen 41' which communicates with both the dilation balloon 18 and the fixation balloon 20 and an outlet port 49' at the proximal end of the outer catheter, wherein a fluid is introduced through the inlet port 40' into the inlet lumen 39' to inflate both the dilation balloon 18 and the fixation balloon 20, and wherein both the dilation balloon 18 and the fixation balloon 20 are subsequently deflated by withdrawing the fluid through the outlet lumen 41' and out the outlet port 41'.

A valve means 58 can also be provided in the inlet lumen 39', such that the valve means 58 is situated between a first opening therein communicating with the fixation balloon 20 and a second opening therein communicating with the dilation balloon 18, as shown in FIG. 4e, and such that said valve means 58 is initially maintained in a first position (in direction of arrow) wherein it closes the inlet lumen while fluid is first introduced into the inlet lumen, and remains closed until the fixation balloon is fully inflated, whereupon, the valve means is openable to an open position, as shown in FIG. 4e, to allow fluid to flow into and inflate the dilation balloon. This embodiment enables the use of a single inflation fluid lumen for both balloons while still enabling independent inflation of each balloon.

In a preferred alternative embodiment of the apparatus, a cooling fluid or fluids, which are identical to the inflation fluid or fluids utilized to inflate the fixation and dilation balloons and which are at an inlet temperature below the ambient temperature, are dynamically circulated through the inflation lumen(s), into the balloons and out through the drainage lumen(s). There is a holdup volume of fluid in each of the balloons during the circulation to maintain them in inflated condition during the procedure. For this embodiment, there is either a continuous supply of fluid or a closed loop system with external cooling and recirculation. The inflation/cooling fluid circulated through the dilation balloon is in contact with microwave antenna 22 and serves to moderate the antenna surface temperature to prevent overheating of the antenna. Moreover, the circulated inflation/ cooling fluid also functions to cool the surface of the dilation balloon which in turn cools the urothelium 33 and thereby prevents the temperature of the tissue of the urothelium from rising to a level where thermal damage and/or pain to the patient could occur. After attainment of a steady state flow of coolant through the dilation balloon, the coolant temperature and urethral wall temperature are in an equilibrium or near equilibrium situation.

The flow rate of the fluid being circulated and the capacity of the lumens conducting the flow is determined by the amount of cooling required to moderate the antenna surface temperature and maintain the surface temperature of the urothelium below the therapeutic temperature at which tissue damage and cell destruction occur.

The apparatus of the present invention can also be used in conjunction with a number of external means for holding the apparatus relative to the patient to stabilize it even more against inadvertent movement during performance of a procedure. Such means can include taping the proximal end of the apparatus to the patient's leg, attaching the apparatus to a girdle worn by the patient around his waist, or by utilizing an arm with a clamp to fix the apparatus to the operating table.

A method of use of the apparatus in the treatment of diseases of the prostate is now described.

A method for treatment of diseases of the prostate utilizing the apparatus of the present invention generally includes the following steps: (a) An embodiment of the apparatus generally consisting of an outer catheter, heating means, a dilation balloon, a fixation balloon, and temperature sensing means is first inserted into the urethra of a male patient. (b) The outer catheter is advanced through the urethra such that the distal end thereof is located in the prostatic urethra. (c) The fixation balloon is inflated to hold the catheter in position and to prevent dilation of the external sphincter. (d) The dilation balloon is inflated to dilate the prostatic urethra to relieve any obstruction thereof symptomatic of diseases of the prostate, to dilate the bladder neck to further relieve the symptom of inability to urinate, and to compress prostatic tissue in order to restrict blood flow to the prostatic tissue during hyperthermal treatment, thereby reducing the heat sink effect of blood-supplied tissue which absorbs hyperthermal energy applied thereto. This enables both greater uniformity of heating of selected target diseased prostatic tissue and a reduction in the amount of power required to supply an effective amount of hyperthermal energy to selected target disease prostatic tissue in order to produce hyperthermal effects therein. (e) Energy is supplied to the heating means in order to raise the temperature of the selected diseased prostatic tissue and produce hyperthermal effects therein. (f) A coolant fluid is circulated through the lumen in the outer catheter provided therefor and through the dilation balloon in order to cool the urothelium and surrounding tissue and to the fixation balloon to cool the external sphincter. In certain embodiments, the coolant circulated through the dilation and/or fixation balloons may be the same fluid used to inflate these balloons in (c) and (d). (g) The temperature of at least one of the diseased prostatic tissue, surrounding non-diseased prostatic tissue and the outlet coolant is monitored during hyperthermal treatment. The temperature near the surface of the dilation balloon, in contact with the urethral wall, can be measured to indicate the temperature of the urethral wall. At equilibrium, the urethral wall outside the balloon and the circulating coolant inside the balloon attain the same or nearly the same temperature. This temperature can also be measured more conveniently by a temperature probe in the outlet coolant stream from the dilation balloon in those embodiments wherein a coolant is circulated through the dilation balloon. At equilibrium, the coolant outlet temperature gives an accurate measure of the temperature at the urethral wall. Alternatively, the rectal wall temperature can be measured using a separate rectal temperature probe. The measured temperature, either urethral wall, coolant outlet (as a measure of urethral wall temperature), or rectal wall temperature, in turn, is used, by means of temperature correlations, to determine the temperature attained in the target prostatic tissue. (h) The amount of energy supplied to the heating means is controlled in response to temperature measurements such that the temperature of the urethral wall, the coolant outlet temperature, or the rectal wall temperature is not allowed to rise to a temperature where damage to non-target tissue can occur, while ensuring the attainment of an appropriate temperature to accomplish the objectives of attaining a sufficiently high temperature in the diseased prostatic tissue in order to produce a hyperthermally induced cell change thereof. Temperature monitoring also enables attainment of an optimum level of energy consumption and by controlling coolant flow and the amount of energy supplied to the heating means, prevents overheating of the heating means. (i) Application of hyperthermal energy to the diseased prostatic tissue is terminated after a sufficient time to produce therapeutic results. (j) The circulation of the coolant fluid through the catheter and dilation balloons is terminated. (k) The dilation balloon is deflated. (l) The fixation balloon is deflated. (m) The catheter is withdrawn from the bladder, bladder neck and prostatic urethra, and is removed from the patient via the urethra.

Where the apparatus further includes suction means detachably coupled to a port in the outer catheter cooperating with the lumen for fluid drainage provided therein, the method further includes the step, performed between steps (e) and (i), above, of (e') utilizing the suction means to evacuate blood, urine, and extracellular fluids through the drainage lumen in the outer catheter during hyperthermal treatment.

Steps (e) through (h) inclusive are performed continuously for a specified period of time and substantially simultaneously with one another.

The following description is referenced to the apparatus depicted in the drawings.

Before insertion into the urethra 11, the apparatus 1 is in a first state wherein dilation balloon 18 and fixation balloon 20 are completely deflated and collapsed against the exterior of outer catheter 12. Microwave antenna 22 is axially mounted within the entire length of the distal end of outer catheter 12 and is surrounded by deflated dilation balloon 18.

The apparatus 1 is guided into and along the urethra. To facilitate insertion, the apparatus 1 may be guided over a previously inserted guide wire (not illustrated) or drainage lumen 34 may contain a guide wire to increase the stiffness of apparatus 1.

The apparatus 1 is advanced within the urethra 11, into the prostatic urethra 9 into and through the bladder neck 17 and into the bladder 14 such that the dilation balloon 18 is positioned in proximity with the transverse lobes 16a, b and median lobe 16e of the prostate 15. FIG. 1 shows the position of the dilation balloon 18 relative to the transverse lobes 16a, b and median lobe 16e of the prostate 15, the bladder neck 17 and bladder 14, the pubic bone 19 and the external sphincter 21 situated in the pelvic floor. The fixation balloon 20 is, at the same time, properly located in the bulbous urethra. The doctor determines that the apparatus 1 is properly positioned by rectally palpating the protuberance 37 circumferentially located on outer catheter 12 at a position before fixation balloon 20 in a direction towards the proximal end of outer catheter 12. The position of the apparatus 1 can also be determined by fluoroscopic or ultrasonic means.

When the apparatus 1 is correctly positioned, the fixation balloon 20 is inflated with inflation fluid through fixation lumen 50. The inflation fluid fills the fixation balloon 20. The inflated fixation balloon 20 causes the apparatus 1 to be fixed such that the dilation balloon 18 and the microwave antenna 22 are in the prostatic urethra 9. For inflation of the fixation balloon 20, an inlet port on the fixation lumen 50 is connected to an inflating means, such as a syringe, and the inflation fluid is injected to inflate the fixation balloon 20 by fluid pressure.

When the inflated fixation balloon 20 is properly located at the bulbous urethra proximal to the external sphincter 21, the doctor knows that the dilation balloon 18 is at its proper location at the prostatic urethra 9 since the fixation balloon 20 of the apparatus 1 is positioned along the catheter tube 12 at a distance from the dilation balloon 18 such that when fixation balloon 20 is at the bulbous urethra, then the dilation balloon 18 is at the prostatic urethra 9. Because the apparatus 1 has such a configuration, inadvertent dilation of the external sphincter 21 and the possible harmful effects consequent therefrom are avoided.

The dilation balloon 18 is then inflated with an inflation fluid through dilation lumen 38. The inflation fluid used to inflate the dilation balloon 18 can be the same as or different than the inflation fluid used to inflate the fixation balloon. Alternatively, both the dilation and fixation balloons can be inflated simultaneously with the same inflation fluid. Preferably, the inflation fluid used to inflate the dilation balloon 18 is deionized water, mineral oil or other suitable fluids with low dielectric properties which act to reduce refracted microwave energy and facilitate coupling of the microwave energy emitted from the surface of microwave antenna 22 into the prostatic tissue. For inflation of the dilation balloon 18, an inlet port on the dilation lumen 38 is connected to an inflating means and the inflation fluid is injected to inflate the dilation balloon 18 by fluid pressure. Where static inflation of the balloons is desired, a fixed volume of inflation fluid is delivered to each balloon with a device such as a syringe. Where dynamic inflation of the balloons is desired, that is, where the balloons are able to be maintained in an inflated state with a steady state circulation of inflation fluid which also acts as a coolant, a metering pump is used to deliver a constant flow of cooled fluid to the balloons, equal to the amount of warm fluid continuously being withdrawn.

In a preferred embodiment of the apparatus 1, the dilation balloon 18 is made of limited distensible material, which causes the balloon to expand upon inflation to a predetermined maximum diameter.

Expansion of dilation balloon 18 causes the dilation balloon to exert pressure against the obstructive prostatic tissue in the prostatic urethra, thereby causing a widening of the prostatic urethra to an unobstructed diameter which relieves the symptoms of an enlarged prostate. Expansion of that portion of the dilation balloon which extends through the bladder neck 17 also dilates the bladder neck which further relieves the symptoms of an enlarged prostate. The pressure exerted on the prostatic tissue also creates a reduction in blood flow to the tissue which is beneficial during the hyperthermia part of the treatment procedure when microwave energy is applied to the prostatic tissue.

The combined treatment procedure is completed, when the dilation balloon 18 has been allowed to remain expanded for an effective period of time to cause a widening of the prostatic urethra, and when an effective amount of microwave energy has been applied to the surrounding diseased prostatic tissue to cause hyperthermal effects.

Microwave antenna 22 is de-energized to terminate radiation of energy to the surrounding prostatic tissue. Dilation balloon 18 and fixation balloon 20 are then deflated by draining the inflation fluid therefrom and out through the drainage lumens. The apparatus is then in condition for withdrawal.

Although the apparatus and method of its use principally discussed hereinabove relates to the treatment of prostate disease, it is not intended that the scope of the invention be limited to treatment of prostate disease, and it will be evident to one of skill in the art that the device and method disclosed herein are also applicable to the treatment of other conditions in which it is desired to simultaneously hyperthermally treat diseased target tissue in a patient while simultaneously effecting dilation of a lumen of a patient which has been compressed and obstructed by the diseased target tissue and/or surrounding tissue.

Such other conditions may include, but are not limited to, tumors of the esophagus and gastro-intestinal tract. It will be evident that appropriate adjustment in the dimensions of the apparatus may be required for use in treatment of other conditions to adapt it to the prevailing anatomical dimensions.

We claim:

1. A method for treatment of conditions in which it is desired to simultaneously hyperthermally treat diseased target tissue in a patient and dilate a lumen of a patient which is being compressed and obstructed by said diseased target tissue and surrounding tissue, said method comprising the steps of:

(a) inserting into the lumen of the patient an apparatus comprising:

(a.i) an outer catheter having a distal end, a proximal end having a plurality of ports therein, and a plurality of lumens situated through said outer catheter, said lumens including a lumen adapted for carrying heating means, inlet and outlet lumens respectively adapted for carrying a fluid into and out of at least one of an inflatable dilation balloon and an inflatable fixation balloon, said fluid being for the inflation of said balloons and alternatively also for acting as a coolant; and up to one or more separate lumens adapted for performing one or more of the functions of carrying temperature sensing means; circulating a coolant fluid through the outer catheter when said fluid for the inflation of said dilation and fixation balloons is not also a coolant; carrying catheter guiding means; and for drainage of fluid; such that there is a corresponding port in said proximal end of said outer catheter which cooperates with each lumen in said outer catheter;

(a.ii) an inner catheter member, mounted in said outer catheter, and having a distal end, a proximal end, and a plurality of lumens therethrough;

(a.iii) heating means, axially mounted at said distal end of said inner catheter member and extending within one of said plurality of lumens in said inner catheter member provided therefor, said heating means being for applying energy to selected target tissue to produce hyperthermal effects therein, thereby causing a therapeutic alteration of cells in said target tissue;

(a.iv) an inflatable dilation balloon mounted at the distal end of the outer catheter for accomplishing at least one of the functions of enlarging an obstructed lumen in the vicinity of said target tissue by compressing obstructive tissue, and restricting blood flow to at least one of said target tissue and to non-target tissue in the vicinity of said target tissue, in order to reduce the energy absorbing heat sink effect produced by blood-enriched tissue, thereby causing a more complete and more uniform absorption of energy by said target tissue;

said dilation balloon having a preform diameter, and an oriented diameter greater than said preform diameter, such that the ratio of the oriented diameter to the preform diameter is from about 4.0 to about 7.0; said dilation balloon also having a preform length and an oriented length greater than said preform length, such that the ratio of the oriented length to the preform length is from about 1.5 to about 3.0; said dilation balloon being fabricated from a material which imparts sufficient hoop strength and burst pressure to the balloon to enable it to perform its intended function, while being bio-compatible and having sufficient softness and pliability to prevent damage to non-target tissue with which it comes into contact;

(a.v) an inflatable fixation balloon mounted within the distal end of said outer catheter adjacent to said dilation balloon, a distance along the length of said outer catheter in a direction toward the proximal end of said outer catheter; said fixation balloon having a preform diameter, and an oriented diameter greater than said preform diameter, such that the ratio of the oriented diameter to the preform diameter is from about 4.0 to about 7.0; said fixation balloon also having a preform length and an oriented length greater than said preform length, such that the ratio of the oriented length to the preform length is from about 1.5 to about 3.0; said fixation balloon being fabricated from a material which imparts sufficient hoop strength and burst pressure to the balloon to enable it to perform its intended function, while being bio-compatible and having sufficient softness and pliability to prevent damage to tissue with which it comes into contact;

(a.vi) temperature sensing means disposed in a manner selected from the group consisting of being carried in a lumen in said outer catheter and mounted on said dilation balloon, said temperature sensing means further including a temperature signal transmitting lead attached at one end thereof to said temperature sensing means, said lead passing through a lumen in said outer catheter provided therefor, and exiting from said proximal end of said outer catheter, at which an opposite end of said lead is connected to means for indicating temperature readings measured by said temperature sensing means; and (a.vii) at least one fluid for inflating said dilation balloon and said fixation balloon, said at least one fluid for inflating said dilation balloon and said fixation balloon being carried into said dilation balloon and said fixation balloon through at least one inlet lumen in said outer catheter and out of said dilation balloon and said fixation balloon through at least one outlet lumen in said outer catheter;

(b) advancing said outer catheter through said lumen of the patient such that the distal end thereof is located in said lumen of the patient in the vicinity of said target tissue to be treated;

(c) inflating the fixation balloon to hold said outer catheter in position;

(d) inflating the dilation balloon to accomplish at least one of the functions of dilating said lumen of the patient in the vicinity of said target tissue to relieve any constriction therein and compressing tissue in order to restrict blood flow to said tissue during hyperthermal treatment, thereby reducing the heat sink effect of blood-supplied tissue which absorbs hyperthermal energy applied thereto, thereby enabling both greater uniformity of heating of selected target tissue and a reduction in the amount of power required to supply an effective amount of hyperthermal energy to said selected target tissue in order to produce hyperthermal effects therein;

(e) supplying energy to the heating means in order to raise the temperature of the selected target tissue and produce hyperthermal effects therein;

(f) circulating a coolant fluid through the lumen in the outer catheter provided therefor and through the dilation and fixation balloons in order to accomplish at least one of the functions of cooling surrounding tissue, and preventing overheating of the surface of the heating means;

(g) monitoring the temperature of at least one of the target tissue, surrounding non-diseased tissue, and the outlet temperature of the coolant fluid during hyperthermal treatment in order to ensure accomplishment of at least one of attaining a sufficiently high temperature in the target tissue in order to produce a hyperthermally induced changes in the cells thereof, to prevent the attainment of a cell damaging hyperthermal temperature in surrounding, non-target tissue, and to prevent overheating of the heating means and attain an optimum level of energy consumption;

(h) controlling the amount of energy supplied to the heating means in response to temperature measurements;

(i) terminating application of hyperthermal energy to said diseased target tissue after a sufficient time to produce therapeutic results;

(j) terminating the circulation of the coolant fluid through the outer catheter, the dilation balloon and the fixation balloon;

(k) deflating the dilation balloon;

(l) deflating the fixation balloon; and (m) withdrawing the apparatus from the lumen of the patient.

2. The method according to claim 1, adapted for use in the treatment of diseases of the prostate, wherein said lumen of a patient is the male urethra; said target tissue is diseased prostatic tissue; said lumen of the patient in the vicinity of said target tissue is at least one of the prostatic urethra and the bladder neck; inflation of said fixation balloon further prevents dilation of the external sphincter of the patient; and said surrounding tissue cooled by circulation of said coolant fluid includes the urothelium and the external sphincter.

3. The method according to claim 2 wherein both the prostatic urethra and bladder neck are simultaneously dilated and selected diseased target tissue is hyperthermally heated.

4. A method for protecting the external sphincter against thermal damage during hyperthermal treatment of the prostate according to the method of claim 2, said method for protecting the external sphincter comprising:

positioning said fixation balloon of the apparatus on the proximal side of said external sphincter;

positioning said dilation balloon of the apparatus on the distal side of said external sphincter;

circulating said inflation fluid, with said inflation fluid also being a coolant, through said fixation balloon and said dilation balloon to thereby inflate said fixation balloon and said dilation balloon, and simultaneously cool an outer surface of each of said fixation balloon and said dilation balloon;

such that when said fixation balloon and said dilation balloon are inflated, at least a portion of said outer surface of said fixation balloon is in contact with at least a portion of said external sphincter on its proximal side, and at least a portion of said outer surface of said dilation balloon is in contact with at least a portion of said external sphincter on its distal side;

and further such that said fluid being circulated through each of said fixation balloon and said dilation balloon causes a cooling of said portions of said external sphincter, which are adjacent on its proximal and distal sides, respectively, to said portions of said outer surfaces of said fixation balloon and said dilation balloon.

5. The method according to claim 1 wherein the apparatus further comprises suction means detachably coupled to a port in the outer catheter cooperating with the lumen for fluid drainage provided therein, further comprising the step, performed between steps (e) and (i) of:

(e') utilizing the suction means to evacuate at least one fluid selected from the group consisting of blood, urine, and extracellular fluids through the drainage lumen in the outer catheter during hyperthermal treatment.

6. The method according to claim 1 wherein steps (e) through (h) inclusive are performed continuously for a specified period of time and substantially simultaneously with one another.

7. An apparatus for treatment of conditions in which it is desired to simultaneously hyperthermally treat diseased tissue in a patient and dilate a lumen of a patient which is being compressed and obstructed by diseased target tissue and/or surrounding tissue, said apparatus comprising:

(a) an outer catheter having a distal end, a proximal end having a plurality of ports therein, and a plurality of lumens situated through said outer catheter, said lumens including a lumen adapted for carrying heating means, inlet and outlet lumens respectively adapted for carrying a fluid into and out of at least one of an inflatable dilation balloon and an inflatable fixation balloon, said fluid being for the inflation of said balloons and alternatively also for acting as a coolant; and up to one or more separate lumens adapted for performing one or more of the functions of carrying temperature sensing means; circulating a coolant fluid through the outer catheter when said fluid for the inflation of said dilation and fixation balloons is not also a coolant; carrying catheter guiding means; and for drainage of fluid; such that there is a corresponding portion of said proximal end of said outer catheter which cooperates with each lumen in said outer catheter;

(b) an inner catheter member, mounted in said outer catheter, and having a distal end, a proximal end, and a plurality of lumens therethrough;

(c) heating means, axially mounted at said distal end of said inner catheter, and extending within one of said plurality of lumens in said inner catheter member provided therefor, said heating means being for applying energy to selected diseased target tissue to produce hyperthermal effects therein, thereby causing a therapeutic alteration of cells in said target tissue;

(d) an inflatable dilation balloon mounted at the distal end of the outer catheter for accomplishing at least one of the functions of enlarging an obstructed lumen in the vicinity of said target tissue by compressing obstructive tissue, and restricting blood flow to at least one of said target tissue and to non-target tissue in the vicinity of said target tissue, in order to reduce the energy absorbing heat sink effect produced by blood-enriched tissue, thereby causing a more complete and more uniform absorption of energy by said target tissue;

said dilation balloon having a preform diameter, and an oriented diameter greater than said preform diameter, such that the ratio of the oriented diameter to the preform diameter is from about 4.0 to about 7.0; said dilation balloon also having a preform length, such that the ratio of the oriented length to the preform length is from about 1.5 to about 3.0; said dilation balloon being fabricated from a material which imparts sufficient hoop strength and burst pressure to the balloon to enable it to perform its intended function, while being bio-compatible and having sufficient softness and pliability to prevent damage to non-target tissue with which it comes into contact;

(e) an inflatable fixation balloon mounted within the distal end of said outer catheter adjacent to said dilation balloon, a distance along the length of said outer catheter in a direction toward the proximal end of said outer catheter; said fixation balloon having a preform diameter, and an oriented diameter greater than said preform diameter, such that the ratio of the oriented diameter to the preform diameter is from about 4.0 to about 7.0; said fixation balloon also having a preform length and an oriented length greater than said preform length, such that the ratio of the oriented length to the preform length is from about 1.5 to about 3.0; said fixation balloon being fabricated from a material which imparts sufficient hoop strength and burst pressure to the balloon to enable it to perform its intended function, while being bio-compatible and having sufficient softness and pliability to prevent damage to tissue with which it comes into contact;

(f) temperature sensing means disposed in a manner selected from the group consisting of:

being carried in a lumen in said outer catheter; and mounted on said dilation balloon, said temperature sensing means further including a temperature signal transmitting lead attached at one end thereof to said temperature sensing means, and at an opposite end thereof to means for indicating temperature readings measured by said temperature sensing means; and (g) at least one fluid for inflating said dilation balloon and said fixation balloon, said at least one fluid for inflating said dilation balloon and said fixation balloon being carried into said dilation balloon and said fixation balloon through at least one inlet lumen in said outer catheter and out of said dilation balloon and said fixation balloon through at least one outlet lumen in said outer catheter.

8. The apparatus according to claim 7 wherein said heating means is selected from the group consisting of a microwave energy transmitting antenna and a radio frequency (RF) energy transmitting antenna.

9. The apparatus according to claim 8 wherein the heating means is a microwave energy transmitting antenna.

10. The apparatus according to claim 8 wherein at least one of said outer catheter and said dilation balloon is covered in selected parts with a material selected from the group consisting of microwave or frequency energy absorbing material, and a microwave or radio frequency energy reflecting material, in order to attenuate microwave or radio frequency energy radiated from said heating means in directions corresponding to those selectively covered parts of said at least one of said outer catheter and said dilation balloon to prevent the temperature in non-target tissue from reaching a damaging level.

11. The apparatus according to claim 7 wherein at least one of said plurality of lumens of said inner catheter member is a coolant lumen surrounding said lumen for said heating means.

12. The apparatus according to claim 11 wherein said inner catheter member has at least one lumen for inflow of coolant and at least one lumen for outflow of coolant, said at least one lumen for inflow of coolant communicating with said at least one lumen for outflow of coolant in at least one location at said distal end of said inner catheter member, to enable a circulation of coolant through said apparatus.

13. The apparatus according to claim 11 wherein said lumen for said heating means and said coolant lumen are the same.

14. The apparatus according to claim 7 wherein said dilation balloon and said fixation balloon are preformed together in a single-piece unit having a collar of specified length interspersed between and connecting said balloons.

15. The apparatus according to claim 7 wherein said temperature sensing means is selected from the group consisting of a thermocouple, a thermistor and a fiber-optic temperature sensor.

16. The apparatus according to claim 15 wherein when said temperature sensing means is a thermocouple, said thermocouple has a heat-conducting metallic element attached to at least a portion of the inflated outer surface area of said dilation balloon.

17. The apparatus according to claim 7 wherein said fixation balloon and said dilation balloon are attached to said outer catheter by bonding thereto.

18. The apparatus according to claim 7 wherein said fixation balloon and said dilation balloon are fabricated from a material selected from the group consisting of polyethylene, polyvinyl chloride, polyester, polyurethane, polyether ether ketone and a silicone elastomer.

19. The apparatus according to claim 18 wherein the material is low density polyethylene.

20. The apparatus according to claim 7 further comprising guidance means mounted in said outer catheter, for guiding said apparatus during its emplacement in said lumen of said patient, which is being compressed and obstructed, and is to be dilated.

21. The apparatus according to claim 20 wherein said guidance means is a guidewire situated in a lumen in said outer catheter provided therefor.

22. The apparatus according to claim 7 wherein said plurality of lumens in said outer catheter are situated axially through said outer catheter; and said plurality of lumens in said inner catheter member are situated axially through said inner catheter member.

23. The apparatus according to claim 7 wherein said outer catheter is flexible.

24. The apparatus according to claim 7 further comprising suction means detachably coupled to a port in said outer catheter cooperating with a lumen for fluid drainage provided in said outer catheter.

25. The apparatus according to claim 7 wherein said lumen for said heating means is centrally located in said inner catheter member.

26. The apparatus according to claim 7 wherein said inner catheter member is independently slidably mounted in said outer catheter.

27. The apparatus according to claim 7, wherein the outer catheter is formed in a plurality of interconnecting and interlocking pieces.

28. The apparatus according to claim 27 wherein the outer catheter is formed of three interconnecting and interlocking pieces.

29. The apparatus according to claim 7 wherein said lumen for said heating means is asymmetrically located in said inner catheter member.

30. An apparatus for treatment of conditions in which it is desired to simultaneously hyperthermally treat diseased target tissue in a patient and dilate a lumen of a patient which is being compressed and obstructed by diseased target tissue and/or surrounding tissue, said apparatus having an overall proximal end and an overall distal end, with said apparatus comprising:

(a) an outer catheter having a distal end, a proximal end having a plurality of ports therein, and a plurality of lumens situated through said outer catheter, said lumens including a lumen adapted for carrying heating means, lumens adapted for carrying a fluid into and out of at least one of an inflatable dilation balloon and an inflatable fixation balloon, said fluid being for the inflation of said balloons and alternatively also for acting as a coolant; and up to one or more separate lumens adapted for performing one or more of the functions of carrying temperature sensing means; circulating a coolant fluid through the outer catheter when said fluid for the inflation of said dilation and fixation balloons is not also a coolant; carrying catheter guiding means; and for drainage of fluid; such that there is a corresponding port in said proximal end of said outer catheter which cooperates with each lumen in said outer catheter, and further such that said outer catheter is fabricated in a plurality of interconnectable subsections, including at least a first subsection and a last subsection, and up to a plurality of intermediate subsections, with each subsection having a proximal end and a distal end, such that said proximal end of said first subsection is situated at said overall proximal end of said apparatus, said distal end of said last subsection is situated at said overall distal end of said apparatus; and said proximal end of any of said plurality of intermediate subsections is in communication with said distal end of another one of said subsections to which it is immediately adjoining, beginning with said distal end of said first subsection; and said distal end of any of said plurality of intermediate subsections is in communication with said proximal end of another one of said subsections to which it is immediately adjoining, ending with said proximal end of said last subsection; and further such that when there are no intermediate subsections, said distal end of said first subsection is in communication with said proximal end of said last subsection; with said subsections being configured such that while the internal path of lumens through any subsection may be the same as or different from the internal path of lumens through other subsections with which it is in communication, each said subsection is fabricated to have a configuration of lumens at its said proximal end and its said distal end which is identical to the configuration of lumens at the proximal end and the distal end of each other subsection, so that each subsection is interchangeable with and interconnectable to one another;

(b) heating means, axially mounted within the distal end of the outer catheter in the lumen provided therefor, for applying energy to selected diseased target tissue to produce hyperthermal effects therein, thereby causing a therapeutic alteration of cells in said target tissue;

(c) an inflatable dilation balloon mounted at the distal end of the outer catheter for accomplishing at least one of the functions of enlarging an obstructed lumen in the vicinity of said target tissue by compressing obstructive tissue, and restricting blood flow to at least one of said target tissue and to non-target tissue in the vicinity of said target tissue, in order to reduce the energy absorbing heat sink effect produced by blood-enriched tissue, thereby causing a more complete and more uniform absorption of energy by said target tissue;

said dilation balloon having a preform diameter, and an oriented diameter greater than said preform diameter, such that the ratio of the oriented diameter to the preform diameter is from about 4.0 to about 7.0; said dilation balloon also having a preform length and an oriented length greater than said preform length, such that the ratio of the oriented length to the preform length is from about 1.5 to about 3.0; said dilation balloon being fabricated from a material which imparts sufficient hoop strength and burst pressure to the balloon to enable it to perform its intended function, while being bio-compatible and having sufficient softness and pliability to prevent damage to non-target tissue with which it comes into contact;

(d) an inflatable fixation balloon mounted within the distal end of said outer catheter adjacent to said dilation balloon, a distance along the length of said outer catheter in a direction toward the proximal end of said outer catheter; said fixation balloon having a preform diameter, and an oriented diameter greater than said preform diameter, such that the ratio of the oriented diameter to the preform diameter is from about 4.0 to about 7.0; said fixation balloon also having a preform length and an oriented length greater than said preform length, such that the ratio of the oriented length to the preform length is from about 1.5 to about 3.0; said fixation balloon being fabricated from a material which imparts sufficient hoop strength and burst pressure to the balloon to enable it to perform its intended function, while being bio-compatible and having sufficient softness and pliability to prevent damage to tissue with which it comes into contact;

(e) temperature sensing means disposed in a manner selected from the group consisting of:

being carried in a lumen in said outer catheter; and mounted on said dilation balloon said temperature sensing means further including a temperature signal transmitting lead attached at one end thereof to said temperature sensing means, and at an opposite and thereof to means for indicating temperature readings measured by said temperature sensing means; and (f) at least one fluid for inflating said dilation balloon and said fixation balloon, said at least one fluid for inflating said dilation balloon and said fixation balloon being carried into said dilation balloon and said fixation balloon through at least one inlet lumen in said outer catheter and out of said dilation balloon and said fixation balloon through at least one outlet lumen in said outer catheter, such that said at least one inlet lumen of said outer catheter and said at least one outlet lumen of said outer catheter each constitute at least one of said plurality of lumens situated through said outer catheter.

31. The apparatus according to claim 30 wherein said at least one inlet lumen is a single inlet lumen having a first opening therein which communicates with said dilation balloon, a second opening therein which communicates with said fixation balloon, and an inlet port at said proximal end of said outer catheter; and said at least one outlet lumen is a single outlet lumen having a first opening therein which communicates with said dilation balloon, a second opening therein which communicates with said fixation balloon, and an outlet port at said proximal end of said outer catheter;

such that there is one said inflation fluid which is introduced through said inlet port into said inlet lumen and into said dilation balloon and said fixation balloon through said first and second openings therein to inflate both said dilation balloon and said fixation balloon, and further such that both said dilation balloon and said fixation balloon are subsequently deflated by withdrawing said fluid through said first and second openings in said outlet lumen and out said outlet port of said outlet lumen.

32. The apparatus according to claim 31 wherein there is a valve means in said single inlet lumen situated between said first opening therein communicating with said fixation balloon and said second opening therein communicating with said dilation balloon, such that said valve means is initially maintained in a first position wherein it closes said single inlet lumen while fluid is first introduced into said single inlet lumen, and remains closed until said fixation balloon is fully inflated, whereupon, said valve means is openable to allow fluid to flow into and inflate said dilation balloon.

33. The apparatus according to claim 31 wherein said fluid used to inflate said dilation balloon are fixation balloon is at a temperature below the ambient temperature of its surroundings to thereby act as a coolant by absorbing heat transferred to it from its surroundings.

34. The apparatus according to claim 33 wherein after both said fixation balloon and said dilation balloon are inflated, an amount of fluid is withdrawn through said outlet lumen while an equal amount of fluid simultaneously enters said inlet lumen so that said fixation balloon and said dilation balloon are maintained in an inflated state, while a steady state circulation of fluid, acting as a coolant, is maintained therethrough.

* * * * *